(12) United States Patent
Britva et al.

(10) Patent No.: US 9,545,529 B2
(45) Date of Patent: Jan. 17, 2017

(54) CONCURRENT TREATMENT WITH THERMAL AND ACOUSTIC ENERGY

(75) Inventors: Alexander Britva, Migdal Ha'Emek (IL); Alexander Dverin, Netanya (IL); Ziv Karni, Kfar Shmaryahu (IL)

(73) Assignee: ALMA LASERS LTD., Caesarea (IL)

( * ) Notice: Subject to any disclaimer, the term of this patent is extended or adjusted under 35 U.S.C. 154(b) by 147 days.

(21) Appl. No.: 14/118,559

(22) PCT Filed: May 17, 2012

(86) PCT No.: PCT/IB2012/052497
§ 371 (c)(1),
(2), (4) Date: Nov. 19, 2013

(87) PCT Pub. No.: WO2012/156944
PCT Pub. Date: Nov. 22, 2013

(65) Prior Publication Data
US 2014/0135662 A1     May 15, 2014

Related U.S. Application Data

(60) Provisional application No. 61/487,720, filed on May 19, 2011.

(51) Int. Cl.
*A61N 7/00* (2006.01)
*A61B 18/18* (2006.01)
*A61B 18/00* (2006.01)

(52) U.S. Cl.
CPC ................. *A61N 7/00* (2013.01); *A61B 18/18* (2013.01); *A61B 2018/00023* (2013.01); *A61N 2007/0008* (2013.01)

(58) Field of Classification Search
CPC .. A61N 7/00; A61N 2007/0008; A61B 18/18; A61B 18/00023
See application file for complete search history.

(56) References Cited

U.S. PATENT DOCUMENTS

| | | | |
|---|---|---|---|
| 5,776,092 | A | 7/1998 | Farin et al. |
| 6,235,024 | B1 | 5/2001 | Tu |
| 6,251,110 | B1 | 6/2001 | Wampler |
| 6,562,032 | B1 | 5/2003 | Ellman et al. |

(Continued)

FOREIGN PATENT DOCUMENTS

| | | | |
|---|---|---|---|
| DE | 3707921 | 9/1987 | |
| WO | 9944514 | 9/1999 | |
| WO | WO 2009095894 | * 8/2009 | ............... A61N 7/00 |

OTHER PUBLICATIONS

In international phase application PCT/IB2012/052497: international search report and written opinion, mailed Aug. 29, 2012.

(Continued)

*Primary Examiner* — Bo J Peng

(57) ABSTRACT

Disclosed are methods for treating a volume of material by concurrently conveying acoustic energy and depositing thermal energy using a unipolar RF (radio-frequency) field. Also disclosed are devices suitable for concurrently conveying acoustic energy and depositing thermal energy using a unipolar RF (radio-frequency) field into the same volume of material. In some embodiments, the disclosed methods and devices are implemented for the treatment of subcutaneous fat.

10 Claims, 7 Drawing Sheets

(56) References Cited

U.S. PATENT DOCUMENTS

| | | | |
|---|---|---|---|
| 6,662,054 B2 | 12/2003 | Kreindel et al. | |
| 6,882,884 B1 | 4/2005 | Mosk et al. | |
| 7,250,047 B2 | 7/2007 | Anderson et al. | |
| 7,452,358 B2 | 11/2008 | Stern et al. | |
| 7,481,781 B2 | 1/2009 | Craig et al. | |
| 7,630,774 B2 | 12/2009 | Karni et al. | |
| 7,955,262 B2 | 6/2011 | Rosenberg | |
| 2002/0007200 A1 | 1/2002 | Desinger | |
| 2003/0163131 A1 | 8/2003 | Manna et al. | |
| 2004/0267252 A1 | 12/2004 | Washington et al. | |
| 2006/0036300 A1* | 2/2006 | Kreindel | A61B 18/14 607/99 |
| 2006/0094988 A1* | 5/2006 | Tosaya | A61H 23/0245 601/2 |
| 2007/0239075 A1* | 10/2007 | Rosenberg | A61N 1/0408 601/2 |
| 2011/0213279 A1 | 9/2011 | Britva et al. | |

OTHER PUBLICATIONS

In corresponding EP national phase application EP/12726229 through Jul. 17, 2014 : preliminary amended claims (with and without annotations), office communication, response to office communication.

* cited by examiner

CONCURRENT TREATMENT WITH THERMAL AND ACOUSTIC ENERGY

CROSS REFERENCE TO RELATED APPLICATIONS

This application is a U.S. national stage of International Application No. PCT/IB2012/052497, titled "Concurrent Treatment With Thermal And Acoustic Energy" and filed May 17, 2012, which claims priority to U.S. Provisional Patent Application No. 61/487,720 filed 19 May 2011, titled "Device and Methods Suitable for Treatment of Body Tissue with Radio-Frequency and Ultrasonic Energy" and filed May 19, 2011, each of which is incorporated herein by reference in their entirety.

FIELD AND BACKGROUND OF THE INVENTION

The invention, in some embodiments, relates to the field of treatment of body tissue with energy, and more particularly, but not exclusively, to methods and devices for treatment of subcutaneous fat using a combination of thermal energy deposited using a unipolar RF (radio-frequency) field and acoustic energy, for example for subcutaneous fat reduction.

Adipose tissue comprises primarily adipocytes containing fat together with fibroblasts, macrophages and endothelial cells. In mammals such as humans, one of the main locations of adipose tissue is the hypodermis (subcutaneous tissue) located beneath the skin (epidermis and dermis) that insulates the body core from external temperature changes but most importantly acts as an energy store for the mammal.

Unlike excessive visceral fat, excessive subcutaneous fat (fat in the hypodermis) in humans is not directly associated with pathologies. However, excessive subcutaneous fat is considered to be unaesthetic and it is common for people to try to reduce the amount and distribution of subcutaneous fat to achieve a more aesthetic external appearance. It is often preferred to treat subcutaneous fat by the local application of energy. Specifically, over a series of individual sessions, energy is locally-applied to the hypodermis. Such local application of energy over a series of individual sessions allows different amounts of subcutaneous fat to be removed from the hypodermis at different locations of the body, allowing the body to be shaped to achieve a desired aesthetic appearance.

Treatment of Subcutaneous Fat with Acoustic Energy

One popular mode of locally-applied energy for the treatment of subcutaneous fat is conveying of acoustic energy (for example, using acoustic waves) through a skin layer into the hypodermis, for example as described in patent application publication US 2011/0213279 of the Applicant, which is incorporated herein by reference as if fully set forth herein, as well as the references cited therein. The acoustic radiative surface of a sonotrode functionally associated with an ultrasound transducer is coupled (e.g., by direct contact or by indirect contact through a coupling substance, e.g., a liquid or gel) to a skin surface of a subject to be treated. The ultrasound transducer is activated to generate acoustic waves that are directed by the acoustic radiative surface of the sonotrode through the skin surface to convey acoustic energy into a volume of the hypodermis. It is believed that application of sufficient acoustic energy (in terms of power, intensity and duration) damages and even ruptures the walls of adipocytes in the hypodermis, releasing fat contained therein into the bulk of the hypodermis.

The power of the acoustic waves is chosen so that the acoustic waves convey substantial energy to a depth of about 2 cm past the skin surface. By "substantial energy" is meant sufficient to achieve a desired result in the treatment of subcutaneous fat. Although acoustic compression (longitudinal) waves are typically used, it has been found that acoustic shear (transverse) waves are also effective, as discussed in US 2011/0213279.

Typically, a course of treatment of subcutaneous fat with acoustic energy includes about six individual weekly treatment sessions. In the period between any two individual sessions, the body clears the fat and cell debris released into the bulk of the hypodermis. To treat an area the size of two thighs and a belly, each session has a duration of about 1 hour which is often considered excessively long, tiring both the treated subject and the operator. The only solution for reducing the duration of an individual session is by increasing the power of the acoustic waves and thereby of the acoustic energy conveyed into the hypodermis. However, increasing the power typically leads to deeper penetration into the body of the treated subject which can be dangerous and damaging to other tissue.

Treatment of Subcutaneous Fat with Thermal Energy

Another popular mode of locally-applied energy for the treatment of subcutaneous fat is heating of a volume of the hypodermis by depositing thermal energy by application of RF (radio-frequency) waves through the skin. The manner in which applied RF waves deposit thermal energy into a volume of hypodermis, and the physiological effect such depositing has, depends on the frequency of the RF waves and the manner in which applied.

RF Waves that Produce Electrical Current

One manner of applying RF waves to treat subcutaneous fat is to produce an electric current (ionic movement) in the hypodermis between two electrodes, see for example, US 2007/0239075 or U.S. Pat. No. 6,662,054. Specifically, two electrodes are coupled (e.g., by direct contact or by indirect contact through a coupling substance, e.g., a liquid or gel) with a skin surface and a functionally-associated RF energy source is activated, producing an RF current that passes through the tissue between the two electrodes. Tissue between the electrodes through which the current passes is heated primarily as a result of the electrical resistance of the tissue.

There are a number of limitations of applying RF waves to deposit thermal energy to treat subcutaneous fat by producing an RF current that passes therethrough.

Indiscriminately passing electric current through the body of a person is dangerous and can lead to electrocution or disruption of heart function. Since electrical current passes between the two electrodes, in practical implementations of such methods the two electrodes are maintained close together (typically between 1 and 5 cm) to ensure that the current-path is well-defined and benign.

Generally, the lower the frequency of the RF waves, the more effectively the thermal energy is deposited by the produced RF current passing through the tissue.

It is generally accepted that for depositing thermal energy using such an RF current, RF frequencies up to about 2 MHz are effective and that RF frequencies above 200 MHz provide substantially no heating. The efficacy of depositing thermal energy with a produced RF current falls-off quickly from frequencies of 2 MHz to about 200 MHz. That said, medical regulatory requirements and legal limitations on RF transmission restrict frequencies used in medical treatments to frequencies in the Industrial, Scientific and Medical (ISM) bands. The ISM bands are typically higher than ideal for depositing thermal energy by a current as described above, e.g., 13.560 MHz±7 kHz, 27.120 MHz±163 kHz, 40.68 MHz±20 kHz and, in some localities, 6.780 MHz±15 kHz. Thus, effective implementation of such methods is practically limited to the lower ISM frequency of 6.780 MHz±15 kHz and possibly 13.560 MHz±7 kHz, while at the higher ISM frequencies 27.120 MHz±163 kHz and 40.68 MHz±20 kHz, such methods are inefficient.

The maximal power of the electric current produced as described above is limited by the power that ensures that the skin surface suffers no substantial damage (e.g., burning, ablation), thereby also limiting the inter-electrode distance and the degree of heating of hypodermis that can be achieved using such methods.

The hypodermis, especially a hypodermis containing excessive fat, has a conductivity an order of magnitude lower than that of skin. As a result, most of the current produced as described above passes through the skin and very little current, and therefore power for heating, passes through the hypodermis.

The current that does pass through the hypodermis passes only through the upper few millimeters of the hypodermis and does not lead to substantial deposition of thermal energy deeper in the hypodermis. As noted above, it is not practically possible to increase the amount and depth of thermal energy deposition by increasing the power of the current without damaging the skin.

Despite the severe limitation on the power of the current that can be produced in the hypodermis as described above and the concomitant limitation of the amount of thermal energy deposited, such methods have proven to be not totally ineffective in treating subcutaneous fat in the upper part of the hypodermis due to the structure of the hypodermis. Specifically, a volume of hypodermis comprises mostly poorly conductive adipocytes, substantially globules of poorly-conducting fat with a small amount of conductive cytoplasm surrounded by electrically insulating cell walls, and between the adipocytes a relatively small amount of conductive intercellular fluid. As a result, electric current produced in the hypodermis passes almost entirely through the intercellular fluid. Since the current is limited to the small volume of the intercellular fluid, despite the relatively low current the concomitant local heating is to a relatively high temperature (typically above 65° C.) that is sufficient to substantially damage adjacent adipocyte walls leading to necrosis or apoptosis thereof.

One solution proposed to deposit thermal energy to treat subcutaneous fat found deeper in the hypodermis as well as to drive less current through the skin and more through the hypodermis is to place the two electrodes on either side of a fold of tissue including the skin and hypodermis, see for example, US 2007/0239075 or U.S. Pat. No. 6,662,054. Clearly, such a treatment that includes folding tissue, for example by suction, is unpleasant for both the subject and the person performing the treatment, is not applicable to all body surfaces, and is of limited efficacy.

An interesting variant for the treatment of subcutaneous fat has been described in US 2007/0239075 which teaches a treatment combining acoustic energy and deposited thermal energy by using RF waves between two electrodes to produce a current in the hypodermis as described above.

Therein is reported that the combined cell-wall destroying effects of the two types of energy are particularly effective. The combined treatment still suffers from disadvantages, for example, the inability for treatment of deeper layers of the hypodermis except by folding tissue with the concomitant disadvantages as described above.

Dielectric Heating with RF Waves

Another manner of applying RF waves to treat subcutaneous fat is through dielectric heating to deposit thermal energy directly into a volume of tissue with a unipolar RF field, for instance, as described in U.S. Pat. No. 7,630,774 of the Applicant which is incorporated by reference as if fully set forth herein. An RF applicator including an RF radiative surface is coupled (e.g., contacted) with a skin surface and a RF energy source functionally-associated therewith is activated to produce RF waves. The RF applicator directs RF waves generated by an activated RF energy source to the RF radiative surface to form a unipolar RF field that passes through skin with which the RF radiative surface is coupled. The formed RF field causes dipolar molecules in the tissue, such as water, to rotate thereby depositing thermal energy in the volume of tissue. It is important to note that at lower frequencies a unipolar RF field may also deposit some thermal energy in tissue by other modes, for example by a current related to polarization of the tissue. Such other modes are more significant the lower the frequency of the RF field: progressively less important at greater than 2 MHz, and being insubstantial at frequencies greater than 10 MHz.

Compared to other tissue such as skin and muscle, the hypodermis includes relatively few blood vessels and is therefore not effectively cooled by the body. Typically dielectric heating with a unipolar RF field allows deposition of thermal energy sufficient to raise the temperature of a volume of tissue to about 45° C.-48° C. Although no direct damage is done to the adipocytes in the hypodermis by such heating (as opposed to heating resulting from a current produced as described above), apparently such a temperature increase is sufficient to raise the metabolic rate in the hypodermis to an extent that allows reduction of the amount of fat in the hypodermis, for example, by increasing the rate of flow of bodily fluids through the heated volume of tissue.

In dielectric heating with a unipolar RF field, the greater the power of the RF waves, the deeper the RF field penetrates and consequently, the deeper thermal energy is deposited. Accordingly, the maximal power of the RF waves for dielectric heating is limited to a power that ensures that no substantial damage is done to tissue deeper than the hypodermis. That said, dielectric heating allows treatment of subcutaneous fat in the entire hypodermis (typically to a maximal depth of about 2 cm) and not only in the upper layers thereof as in heating by a produced current as discussed above.

For dielectric heating, the efficiency (proportion of power of the RF waves to thermal energy deposited in the tissue) increases with increasing frequency. Thus although any frequency can be used for dielectric heating of tissue, typically an RF field having a frequency of at least 2 MHz, at least 4 Mhz and even at least 10 MHz is preferred. That said, dielectric heating of hypodermis with a unipolar RF field is most effective at frequencies between 10 MHz and 100 MHz, especially at higher values of this range.

As with treatment with acoustic energy, a typical course of treatment of subcutaneous fat with RF waves, whether for dielectric heating or for heating by an induced current, includes about six individual weekly treatment sessions. To treat an area the size of two thighs and a stomach, each such individual session has a duration of about 1 hour. Analogously to treatment with acoustic energy, the only manner of reducing the duration of a given individual session is by increasing the power of the RF energy source which, as discussed above, is not practical.

It has been proposed during an individual treatment session to first treat a volume of tissue with acoustic energy to damage adipocyte walls and then to deposit thermal energy in the same volume of tissue by dielectric heating to accelerate local metabolism to clear the fat and cell debris released into the volume of tissue by the acoustic energy treatment. In a single such combined session to treat an area the size of two thighs and a belly, the duration of the acoustic treatment is about 1 hour followed by dielectric heating for about 20 to 30 minutes. It has been found that although each such session is of longer duration; such combined treatments provide better results.

SUMMARY OF THE INVENTION

The invention, in some embodiments, relates to the treatment of body tissue with energy and more particularly, but not exclusively, to methods for the treatment of tissue such as subcutaneous fat using a combination of thermal energy and acoustic energy. The invention, in some embodiments, relates to devices for treatment of material with energy and more particularly, but not exclusively, to a device suitable for the treatment of a volume of material with a combination of thermal energy and acoustic energy, for example materials such as hypodermis, especially for the treatment of subcutaneous fat.

Thus, according to an aspect of some embodiments of the invention there is provided a method of treatment of subcutaneous fat in a subject, comprising: concurrently a) conveying an effective amount of acoustic energy into a volume of hypodermis through a skin surface with which an acoustic radiative surface of a sonotrode is coupled; and b) depositing an effective amount of thermal energy into the volume of hypodermis with a unipolar RF field through a skin surface.

According to an aspect of some embodiments of the invention there is also provided a device suitable for treatment of a volume of material with energy through a surface, the device comprising:

an ultrasound transducer functionally associated with a sonotrode having an acoustic radiative surface, the ultrasound transducer configured, when activated, to generate acoustic waves that are directed by the acoustic radiative surface into the volume of material through a first portion of a surface with which the acoustic radiative surface is coupled to convey an effective amount of acoustic energy into the volume of material; and an RF (radio-frequency) applicator having an RF radiative surface, which RF applicator is functionally associable with an RF energy source, the RF applicator configured to direct RF waves, generated by an activated RF energy source functionally-associated with the RF applicator, to the RF radiative surface to form a unipolar RF field, the unipolar RF field passing through a second portion of the surface with which the RF radiative surface is coupled to deposit an effective amount of thermal energy in the volume of material, wherein the device is configured for concurrent depositing of the effective amount of thermal energy and conveying of the effective amount of acoustic energy into the volume of material.

Unless otherwise defined, all technical and scientific terms used herein have the same meaning as commonly understood by one of ordinary skill in the art to which the invention pertains. In case of conflict, the specification, including definitions, will control.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, in some instances (for example in U.S. Provisional Patent Application 61/487,720) the terms "ultrasound radiative surface" and "ultrasonic radiative surface" and variants thereof are substantially synonymous with the term "acoustic radiative surface" and variants thereof.

As used herein, in some instances (for example in U.S. 61/487,720) the phrase "to deliver an effective amount of ultrasonic (mechanical) waves into a volume of material" and variants thereof is substantially synonymous with the phrase "to convey an effective amount of acoustic energy into a volume of material" and variants thereof.

As used herein, in some instances (for example in U.S. 61/487,720) the phrase "to direct an RF alternating electric field into a volume of material so that the RF alternating electric field conveys an effective amount of energy in the volume of material" and variants thereof is substantially synonymous with the phrase "to deposit an effective amount of thermal energy into a volume of material" and variants thereof.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1A:
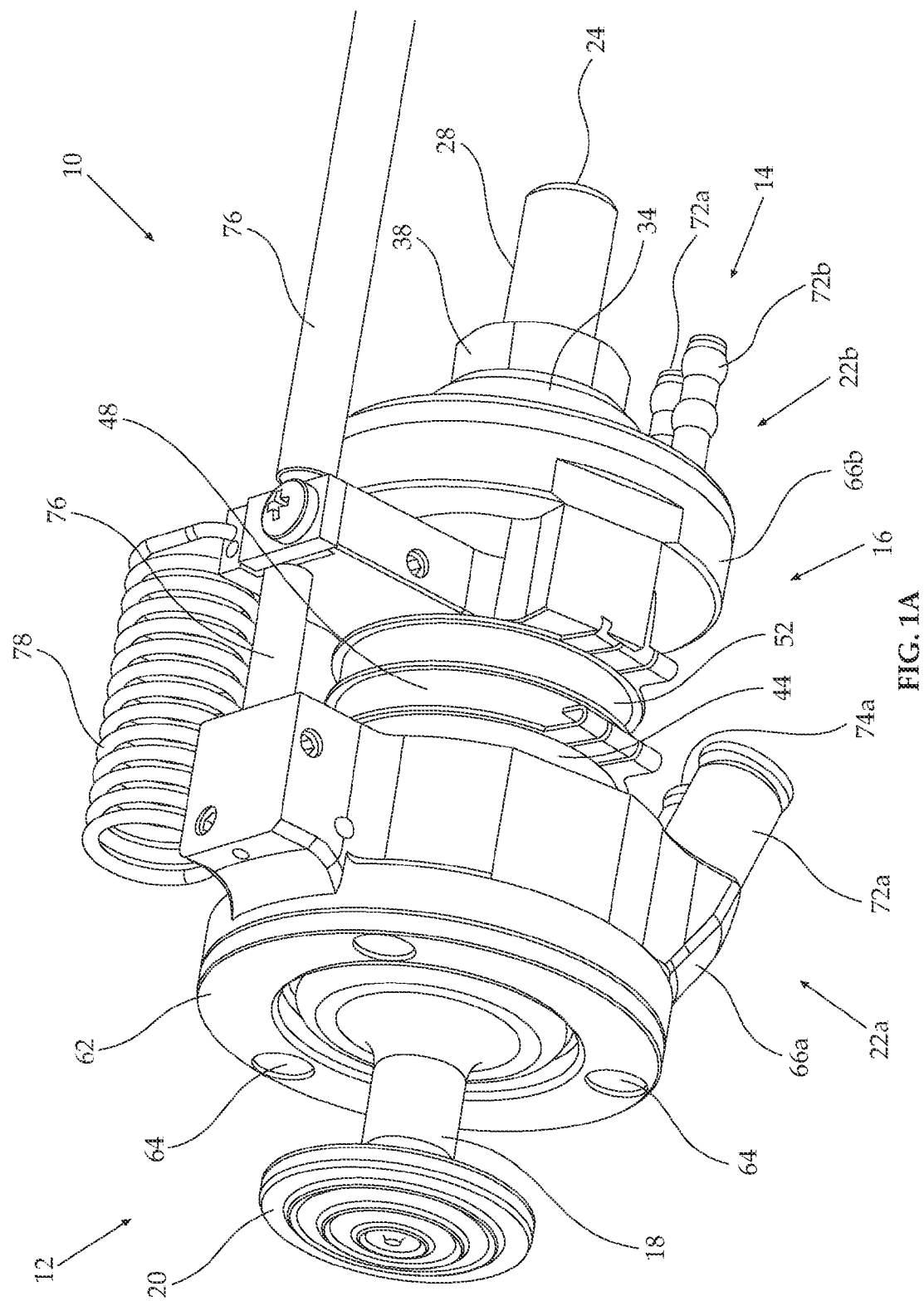
FIG. 1A depicts an embodiment of a device suitable for treatment of a volume of material such as hypodermis according to the teachings herein fully assembled, in perspective from a distal end.

The invention, in some embodiments, relates to the treatment of body tissue with energy and more particularly, but not exclusively, to methods for the treatment of tissue such as subcutaneous fat using a combination of thermal energy and acoustic energy. The invention, in some embodiments, relates to devices for treatment of material with energy and more particularly, but not exclusively, to a device suitable for the treatment of a volume of material with a combination of thermal energy and acoustic energy, for example materials such as hypodermis, especially subcutaneous fat.

The principles, uses and implementations of the teachings herein may be better understood with reference to the accompanying description and figures. Upon perusal of the description and figures present herein, one skilled in the art is able to implement the invention without undue effort or experimentation. In the figures, like reference numerals refer to like parts throughout.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

As discussed above, it is known to use acoustic energy to treat subcutaneous fat by conveying acoustic energy using acoustic waves through the skin into the hypodermis, see for example US 2011/0213279. It is also known to deposit thermal energy into a volume of tissue through dielectric heating with a unipolar RF field to treat subcutaneous fat, see for example U.S. Pat. No. 7,630,774. Such treatments take an excessively long time: as discussed above, a treatment session of an area the size of two thighs and a belly typically takes about an hour.

Increasing the power of such treatments is potentially unsafe, including the possibility of causing excessive damage, including to tissue other than the hypodermis.

As noted above in the introduction, it has been found that serially combining the two treatments, e.g., acoustic energy treatment followed by thermal energy treatment yields improved results but no significant savings in time: as discussed above, such a serial treatment session of an area the size of two thighs and a stomach typically takes about 90 minutes.

Method of Treatment Of Subcutaneous Fat

According to an aspect of some embodiments of the teachings herein, there is provided a method of treatment of subcutaneous fat in a subject, comprising: concurrently a) conveying an effective amount of acoustic energy, for example, generated by an ultrasound transducer, into a volume of hypodermis through a skin surface with which an acoustic radiative surface of a sonotrode is coupled; and b) depositing an effective amount of thermal energy into the volume of hypodermis with a unipolar RF field through a skin surface, so that the heating is primarily by dielectric heating. In some embodiments, the subject is a human. In some embodiments, the subject is a non-human animal.

In some embodiments, conveying of the effective amount of acoustic energy concurrently with the depositing of the effective amount of thermal energy initiates a process leading to a reduction of the amount of fat in the volume of hypodermis.

In some embodiments, the depositing of the effective amount of thermal energy is sufficient to substantially raise (and in some embodiments maintain) the temperature of the volume of hypodermis to a temperature of between 42° C. and 48° C., and in some embodiments between 42° C. and 46° C.

Typically, the method is non-invasive, that is to say the skin surface remains intact, and is not punctured or otherwise penetrated. In some embodiments, the method is a non-surgical method, performed without breaking the skin. Embodiments of the method are performed by any suitable person, including medical personnel but typically aesthetic technicians such as beauticians.

In some embodiments, the concurrent exposure of the same volume of hypodermis to both acoustic energy and thermal energy leads to greater efficacy and/or (surprisingly) shorter treatment times when compared to equivalent treatments by thermal energy alone, acoustic energy alone or serial treatment as described above. For example, in some embodiments, the concurrent exposure of the same volume of a subcutaneous fat layer to both acoustic energy and thermal energy leads to faster treatment for similar effect (e.g., each session of around 30 to 35 minutes instead of 60 minutes) without requiring an increase of power of either modality.

In some embodiments, it has been found that it is possible to reduce the power of the acoustic energy and/or of the RF field when compared to equivalent treatments by thermal energy alone, acoustic energy alone or serial treatment as described above and still achieve comparable or better effects.

Although not wishing to be held to any one theory, it is believed that in some embodiments the walls of adipocytes that are at or maintained at higher than body temperatures (e.g., 42° C.-48° C., more typically 42° C.-46° C.) are more susceptible to damage and disruption by acoustic energy (whether continuously or discontinuously applied acoustic energy) than adipocytes at body temperature.

Although not wishing to be held to any one theory, it is believed that in some embodiments the walls of adipocytes that are subject to repeated variations of temperature (e.g., within a range having a lower value at least of body temperature and an upper value of up to 48° C., more typically up to 46° C.) are more susceptible to damage and disruption by acoustic energy (whether continuously or discontinuously applied acoustic energy) than adipocytes maintained at a constant temperature, especially at a constant temperature near body temperature.

In some embodiments, the concurrent exposure of the same volume of hypodermis to both acoustic energy and thermal energy reduces unwanted side-effects apparent, for example, when treating hypodermis with acoustic energy alone. For example, in some embodiments, the incidence of ovoid adipocytes or lipid lacunae, which appearance is known subsequent to treatment with acoustic energy alone, is reduced.

Generally, conveying acoustic energy into a volume of hypodermis through a skin surface occurs when an acoustic radiative surface of a sonotrode functionally associated with an activated ultrasound transducer is coupled with a skin surface, e.g., the acoustic radiative surface is in direct contact with the skin, or is in indirect contact with the skin, for example, through an impedance-matching material such as an ultrasound gel (e.g., Graham-Field Ultrasound Gel, GF Health Products Inc., Atlanta, Ga., USA) or petroleum jelly.

In some embodiments, the depositing of the effective amount of thermal energy into the volume of hypodermis with a unipolar RF field is effected through a skin surface with which an RF radiative surface of an RF applicator is coupled (e.g., is in direct contact or is in indirect contact with the skin), the RF applicator directing RF waves generated, for example, by an activated RF energy source.

Volume of Hypodermis

The volume of hypodermis to which concurrently an effective amount of acoustic energy is conveyed and an effective amount of thermal energy is deposited is of any suitable size. That said, in typical embodiments the volume is between 7 cm$^3$ and 56 cm$^3$, e.g., a 1 to 2 cm deep cylinder of tissue beneath a skin area of between 7 cm$^2$ (e.g., a circle having a radius of 1.5 cm) and 28 cm$^2$ (e.g., a circle having a radius of 3 cm).

In a manner analogous to that known in the art, during a treatment session of a subject in accordance with the method according to the teachings herein, the location of the volume of hypodermis to which an effective amount of acoustic energy is conveyed and concurrently an effective amount of thermal energy is deposited at any one time is changed, for example, by moving an acoustic radiative surface and an RF radiative surface during a single session to couple to different portions of the skin surface of a subject. Accordingly, in some embodiments, a lubricant material is applied between the skin surface and the radiative surfaces. Often, such a lubricant is selected to also function as an impedance-matching material as noted above.

It is important to note that in some, but not all, embodiments of the method according to the teachings herein, the volume of hypodermis to which both the effective amount of acoustic energy is conveyed and the effective amount of thermal energy is deposited is smaller than the volume of hypodermis to which only an effective amount of acoustic energy is conveyed. Similarly, in some, but not all, embodiments of the method according to the teachings herein, the volume of hypodermis to which both the effective amount of acoustic energy is conveyed and the effective amount of thermal energy is deposited is smaller than the volume of hypodermis to which only an effective amount of thermal energy is deposited.

Shared Radiative Surfaces

In order to increase the intersection of the volume of hypodermis to which the effective amount of acoustic energy is conveyed with the volume of hypodermis in which the effective amount of thermal energy is deposited, in some embodiments, the ultrasound radiative surface and the RF radiative surface are at least partially shared, that is to say, at least a portion of the ultrasound radiative surface constitutes at least a portion of the RF radiative surface. In some such embodiments, at least a portion of the ultrasound radiative surface constitutes the RF radiative surface. In some such embodiments, at least a portion of the RF radiative surface constitutes the ultrasound radiative surface.

Same Radiative Surfaces

In some embodiments, the ultrasound radiative surface and the RF radiative surface are substantially the same radiative surface, that is to say, the ultrasound radiative surface constitutes the RF radiative surface. In such embodiments, the intersection between the volume of hypodermis to which an effective amount of acoustic energy is conveyed and the volume of hypodermis to which an effective amount of thermal energy is deposited is greatest. Further, the volume of hypodermis affected by only one of the two modalities is smallest, reducing the chance of undesired side effects, providing a more homogenous treatment and rendering the method more easily implementable.

Concurrent Conveying of Acoustic Energy and Depositing of Thermal Energy

The method of treating subcutaneous fat described herein comprises concurrently conveying an effective amount of acoustic energy and depositing an effective amount of thermal energy into a volume of hypodermis with a unipolar RF field.

Simultaneous

In some embodiments by concurrent is meant that the conveying of the effective amount of acoustic energy and the depositing of the effective amount of thermal energy is simultaneous.

In some such embodiments, during a period of time, the conveying of the effective amount of acoustic energy is continuous and the depositing of the effective amount of thermal energy is also continuous. It is believed that in such embodiments, the efficacy of the acoustic energy is increased because the volume of hypodermis is maintained at a temperature higher than body temperature.

In some such embodiments, during a period of time (e.g., a period of time having a duration of at least 10 seconds), the conveying of the effective amount of acoustic energy is continuous and the depositing of the effective amount of thermal energy is discontinuous (e.g., at irregular intervals, regular intervals, periodically). In some such embodiments, the depositing of the effective amount of thermal energy is during not less than 30% of the period of time and even not less than 45% of the period of time. In some such embodiments, the effective amount of thermal energy is deposited periodically during the period of time at a rate not slower than 0.2 Hz. In some such embodiments, discontinuous depositing of thermal energy maintains the volume of hypodermis at an elevated (higher than body) temperature. In this context it is important to note that subcutaneous fat is typically less effectively cooled than other tissue such as skin, so that in some embodiments discontinuous depositing of thermal energy allows maintenance of subcutaneous fat at elevated temperatures while reducing the chance that other tissue is adversely effected by the heating. That said, in some such embodiments, discontinuous depositing of thermal energy leads to repeated variations of temperature of the volume of hypodermis. It is believed that in some such embodiments, the efficacy of the conveyed acoustic energy is increased because the adipocytes in the volume of tissue are subject to repeated variation of temperature.

Alternating

In some embodiments by concurrent is meant that the conveying of the effective amount of acoustic energy alternates with the depositing of the effective amount of thermal energy. In some such embodiments, the alternating is at a rate of not slower than 0.2 Hz. In some embodiments, the alternating is at regular intervals, for example, periodic while in some embodiments, the alternating is at irregular intervals. In some such embodiments, such discontinuous depositing of thermal energy maintains the volume of hypodermis at an elevated temperature. Although it is generally accepted in the art that acoustic energy must be continuously conveyed to be effective, it is believed that in some such embodiments, the elevated temperature of the volume of hypodermis renders discontinuous conveying of the acoustic energy effective.

In some such embodiments, discontinuous depositing of thermal energy leads to repeated variations of temperature of the volume of hypodermis. Although it is generally accepted in the art that acoustic energy must be continuously conveyed to be effective, it is believed that in some such embodiments, the varying temperature of the volume of hypodermis renders the discontinuous conveying of the acoustic energy particularly effective.

It is important to note, that in some embodiments, as noted above, that discontinuous depositing of thermal energy reduces the incidence of unwanted side-effects such as burning of the skin without substantially reducing the efficacy of the treatment.

Effective Amount of Acoustic Energy

By an effective amount of acoustic energy is meant intensity and duration of acoustic energy having suitable characteristics (e.g., direction, dispersion, frequency) to lead to a desired effect, such as damage to adipocytes in a hypodermis, e.g., for aesthetic modification. A person having ordinary skill in the art is familiar with or is able to decide or is able to determine without undue experimentation what constitutes an effective amount of acoustic energy in analogy to known commercially-available such treatments. In this context it is important to note that, in some embodiments of the method described herein, the intensity of the acoustic energy conveyed to the volume of hypodermis is reduced compared to comparable known treatments allowing a reduction of unwanted side effects such as unwanted damage to non-adipocyte cells.

Acoustic energy is conveyed with the use of acoustic waves. Acoustic waves having any suitable characteristics may be used in implementing embodiments of the method according to the teachings herein, especially acoustic waves having characteristics known in the art of the treatment of adipose tissue, especially subcutaneous fat such as discussed in US 2011/0213279. Such waves typically have a frequency of between 20 kHz and 100 kHz.

In some embodiments, the effective amount of acoustic energy is conveyed by longitudinal waves.

In some embodiments, the effective amount of acoustic energy is conveyed by transverse waves.

In some embodiments, the effective amount of acoustic energy is conveyed by both longitudinal and transverse waves.

In some embodiments, during a period of time that the method is implemented, the effective amount of acoustic energy is alternately conveyed by longitudinal waves and by transverse waves.

Effective Amount of Thermal Energy

By an effective amount of thermal energy is meant an amount of thermal energy that provides sufficient heating of the volume of hypodermis for an intended purpose, e.g., for aesthetic modification. A person having ordinary skill in the art is familiar with or is able to decide or is able to determine without undue experimentation what constitutes an effective amount of thermal energy, typically an amount of thermal energy sufficient to raise the temperature in the volume of hypodermis to between 42° C. and 48° C.

In this context it is important to note that, in some embodiments of the method described herein, an equivalent desired effect is achieved when the temperature to which the volume of hypodermis is raised is lower than that of comparable known treatments, e.g., to between 42° C. and 46° C., in some embodiments between 42° C. and 45° C. In some embodiments, such lower temperature is achieved by reducing the amount of the thermal energy deposited in the volume of hypodermis when compared to comparable known treatments, allowing a reduction of unwanted side effects such as burning of the skin and unwanted damage to non-adipocyte cells.

To deposit the effective amount of thermal energy, a unipolar RF electric field having any suitable characteristics (e.g., intensity, duration, frequency) is used in implementing embodiments of the method according to the teachings herein, especially a unipolar RF electric field having characteristics known in the art of the treatment of adipose tissue, especially subcutaneous fat layers such as discussed in U.S. Pat. No. 7,630,774.

A unipolar RF field having any suitable frequency may be used for depositing the effective amount of thermal energy, typically a frequency between 3 Hz and 300 GHz. That said, since the preferred mode of depositing thermal energy, in some embodiments it is preferred that the unipolar RF field have a frequency of not less than 2 MHz, not less than 4 MHz and in some embodiments not less than 10 MHz. In typical preferred embodiments, the unipolar RF field has a frequency between 10 MHz and 100 MHz.

That said, due to legal limitations as well as proven efficacy in the field of treating adipose tissue, in some embodiments the unipolar RF field has a frequency in an Industrial, Scientific and Medical (ISM) frequency band. Accordingly, in some embodiments the unipolar RF field has a frequency in a frequency band selected from the group consisting of generally accepted ISM frequency bands (13.560 MHz±7 kHz, 27.120 MHz±163 kHz, 40.68 MHz±20 kHz, 2.45 GHz±50 MHz, 5.800 GHz±75 MHz, 24.125 GHz±125 MHz), frequencies that are subject to local acceptance (6.780 MHz±15 kHz, 61.25 GHz±250 MHz, 122.5 GHz±500 MHz, 245 GHZ±1 GHz), accepted in International Telecommunication Union Region 1 only (Europe, Asia, Africa, excluding the Far-East, Oceania and Australia; 433.92 MHz±870 kHz) and accepted in International Telecommunication Union Region 2 only (the Americas, 915 MHz±13 MHz). That said, in some embodiments the unipolar RF field has a frequency in a frequency band selected from the group of frequency typically used in the field of treatment of adipose tissue, 13.560 MHz±7 kHz, 27.120 MHz±163 kHz, 915 MHz±13 MHz, but most especially 40.68 MHz±20 kHz.

Cooling of a Skin Surface

As is known in the art, depositing an effective amount of thermal energy into a volume of hypodermis through a skin surface to lead to a desired effect such as heating of the hypodermis can lead to undesirable effects such as burning or scorching the skin. Such undesirable effects may be aggravated by the concurrent (especially simultaneous) conveying of acoustic energy as disclosed herein.

In some embodiments, the characteristics of the unipolar RF field are selected to avoid undesirable effects, for example, in accordance with the teachings of U.S. Pat. No. 7,630,774. Alternatively or additionally, in some embodiments a portion of the skin surface of the subject is actively cooled.

In some embodiments, the method further comprises, during the depositing of an effective amount of thermal energy, cooling a portion of a skin surface proximal to the acoustic radiative surface, in some embodiments, thereby effecting cooling of a portion of a skin surface proximal to the acoustic radiative surface. In some such embodiments, the ultrasound radiative surface is cooled, for example by the passage of a cooling fluid in proximity thereto (for example near or through the sonotrode), to effect cooling of the portion of the skin surface.

In some embodiments, the method further comprises, during the depositing of an effective amount of thermal energy, cooling a portion of a skin surface proximal to the RF radiative surface, in some embodiments, thereby effecting cooling of a portion of a skin surface proximal to the RF radiative surface. In some such embodiments, the RF radiative surface is cooled, for example by the passage of a cooling fluid in proximity thereto (for example near or through the RF applicator), to effect cooling of the portion of the skin surface.

Use of Impedance Matching Material

As known in the art, conveying acoustic energy into a volume of tissue such as hypodermis through a skin surface is most effective when contact with the skin is made with the help of an impedance matching material between the skin surface and the ultrasound radiative surface, for example with a fluid material that also acts as a lubricant such as an ultrasound gel (e.g., Graham-Field Ultrasound Gel, GF Health Products Inc., Atlanta, Ga., USA) or petroleum jelly. To assist in preventing current passing from the RF radiative surface to the subject being treated, it is generally preferred that such impedance matching material be non-conductive, for example, petroleum jelly.

The method according to the teachings herein may be implemented using any suitable device. That said, in some embodiments it is preferred to implement the method using a device in accordance with the teachings herein.

Device Suitable for the Treatment of Material Through a Surface

According to an aspect of some embodiments of the teachings herein there is provided a device suitable for treatment of a volume of material, especially of biological tissue, with energy through a surface, the device comprising:

an ultrasound transducer functionally associated with a sonotrode having an acoustic radiative surface, the ultrasound transducer configured, when activated, to generate acoustic waves that are directed by the acoustic radiative surface into the volume of material through a first portion of a surface with which the acoustic radiative surface is coupled to convey an effective amount of acoustic energy into the volume of material; and an RF (radio-frequency) applicator having an RF radiative surface, which RF applicator is functionally associable with an RF energy source, the RF applicator configured to direct RF waves, generated by an activated RF energy source functionally-associated with the RF applicator, to the RF radiative surface to form a unipolar RF field, the unipolar RF field passing through a second portion of the surface with which the RF radiative surface is coupled to deposit an effective amount of thermal energy in the volume of material, primarily by dielectric heating, wherein the device is configured for concurrent depositing of the effective amount of thermal energy and conveying of the effective amount of acoustic energy into the volume of material.

Activation of the ultrasound transducer to generate acoustic waves is as known in the art, typically by providing an appropriately modulated electronic signal from an ultrasound power source to the ultrasound transducer.

In some embodiments, the surface is a skin surface (especially mammalian skin surface) and the material is hypodermis, especially subcutaneous fat. In such embodiments, the conveying of acoustic energy and the depositing of the thermal energy is through the skin. In such embodiments, the device is configured for the treatment of subcutaneous fat. In some such embodiments, the concurrent depositing of an effective amount of thermal energy (that heats the volume of hypodermis) and conveying of the effective amount acoustic energy (that causes mechanical stress on adipocytes in the volume of hypodermis) is sufficient to initiate a process leading to a reduction of the amount of subcutaneous fat in the volume of hypodermis, in some embodiments more effectively than either when applied alone, for example in accordance with the method of treatment of subcutaneous fat according to the teachings herein.

In some embodiments, the sonotrode and the RF applicator are configured so that the volume of material (e.g., hypodermis) is of between 7 $cm^3$ and 56 $cm^3$.

Shared Radiative Surface

As discussed with reference to the method of treatment in accordance with the teachings herein, in some embodiments a radiative surface at least partially shared between the sonotrode and the RF applicator increases the overlap of the volume of material to which an effective amount of acoustic energy is conveyed and the volume of material in which an effective amount of thermal energy is deposited. Accordingly, in some embodiments, at least a portion of the acoustic radiative surface constitutes at least a portion of the RF radiative surface. In some such embodiments, during use of the device the first portion of the (skin) surface through which the acoustic energy is conveyed and the second portion of the (skin) surface through which the thermal energy is deposited at least partially overlap.

In some such embodiments, at least a portion of the acoustic radiative surface constitutes the RF radiative surface. In some such embodiments, during use of the device the second portion of the (skin) surface through which the thermal energy is deposited is a part of the first portion of the (skin) surface through which the acoustic energy is conveyed.

In some such embodiments, at least a portion of the RF radiative surface constitutes the acoustic radiative surface. In some such embodiments, during use of the device the first portion of the (skin) surface through which the acoustic energy is conveyed is a part of the second portion of the (skin) surface through which the thermal energy is deposited.

In some such embodiments, the acoustic radiative surface constitutes the RF radiative surface. In some such embodiments, during use of the device the first portion of the (skin) surface through which the acoustic energy is conveyed is substantially the same as the second portion of the (skin) surface through which the thermal energy is deposited.

In some such embodiments, such a feature is implemented by using a component that functions as both the sonotrode and as the RF applicator of the device, including parts, subcomponents and assemblies that are bifunctional, serving a function as a part of the sonotrode and a function as part of the RF applicator. Some such embodiments allow simple and convenient use, for implementing embodiments of the teachings herein, but also for treatment exclusively by conveying acoustic energy or depositing thermal energy. Accordingly, in some embodiments of the device as described herein, the sonotrode and the RF applicator are the same component.

Rigid RF Applicator

Some RF applicators known in the art are flexible components unsuitable for use as a sonotrode (e.g., a printed circuit board such as described in U.S. Pat. No. 7,452,358) due to the inefficiency of flexible components for conveying acoustic energy. In contrast, in some embodiments of a device herein, and particularly embodiments where at least a portion of the acoustic radiative surface constitutes at least a portion of the RF radiative surface, the RF applicator is sufficiently rigid for conveying the effective amount of acoustic energy. In some such embodiments, the RF applicator is substantially a solid rigid mass of electrically-conductive material.

Concurrent Activation of Ultrasound Transducer and RF Energy Source

In some embodiments, the configuration for concurrent depositing of an effective amount of thermal energy and conveying of an effective amount of acoustic energy includes configuration for concurrent activation of the ultrasound transducer and of a functionally-associated RF energy source.

In some embodiments of a device as described herein, the device is configured so that concurrent activation of the ultrasound transducer and of an RF energy source functionally-associated with the RF applicator is mandatory. In such embodiments, activation of a functionally-associated RF energy source is always concurrent with activation of the ultrasound transducer.

In some embodiments of a device described herein, the device is configured so that concurrent activation of the ultrasound transducer and of an RF energy source functionally-associated with the RF applicator is optional. Typically, such embodiments allow a user to select operation of the device in a "concurrent mode" where the ultrasound transducer and a functionally-associated RF energy source are operated concurrently, and at least one other mode. During operation in "concurrent mode", the ultrasound transducer and a functionally-associated RF energy source are concurrently activated, for example, allowing conveying of acoustic energy with concurrent depositing of thermals energy, for example in accordance with the method of treatment according to the teachings herein.

In some such embodiments of a device where concurrent activation is optional, the device is configured to allow at least two modes of operation: a mode of "acoustic only" where the ultrasound transducer is activated alone (for example, allowing conveying of acoustic energy without concurrent depositing of thermal energy, for example as described in US 2011/0213279) and a "concurrent mode".

In some such embodiments of a device where concurrent activation is optional, the device is configured to allow at least two modes of operation: a mode of "RF only" where a functionally-associated RF energy source is activated alone (for example, allowing depositing of thermal energy alone without concurrent conveying of acoustic energy, for example as described in U.S. Pat. No. 7,630,774) and a "concurrent mode"

In some such embodiments of a device where concurrent activation is optional, the device is configured to allow at least three modes of operation: an "ultrasonic only" mode, an "RF only" mode and a "concurrent mode".

In some embodiments, the device is configured so that the concurrent activation of the ultrasound transducer and of an RF energy source functionally-associated with the RF applicator is at least optionally simultaneous activation, allowing simultaneous conveying of acoustic energy and depositing of thermal energy. In some embodiments, such simultaneous activation is mandatory. In some embodiments, such simultaneous activation is optional, e.g., selected by a user of the device.

In some embodiments, the ultrasound transducer is configured for continuous activation during a period of time (typically at least 10 seconds, more typically at least 5 minutes or for a length of time limited by the user) for continuous conveying of acoustic energy during the period of time; and a functionally-associated RF energy source is configured for discontinuous activation (including at regular or irregular intervals, periodic, non-periodic) during the period of time, for discontinuous depositing of thermal energy. In some such embodiments, discontinuous activation of a functionally-associated RF energy source is periodic activation, in some embodiments at a rate not slower than 0.2 Hz.

In some embodiments, the device is configured so that concurrent activation of the ultrasound transducer and of a functionally-associated RF energy source is at least optionally alternating activation, allowing alternatingly conveying of acoustic energy and depositing of thermal energy during a period of time, in some embodiments the alternating activation is at a rate not slower than 0.2 Hz.

Cooling Assembly

As discussed with reference to the method of treatment in accordance with the teachings herein, depositing thermal energy potentially leads to undesirable side-effects, such as excessive heating and even burning of a surface coupled with the RF radiative surface, for example, burning of a skin surface when a functionally-associated RF energy source is activated. To reduce or avoid the incidence of such undesirable side-effects when the device is used and the RF energy source is activated, in some embodiments the device is configured to actively cool a portion of a surface during treatment of a volume of material with the device.

To this end, in some embodiments, a device further comprises a cooling assembly configured, when activated, to cool at least one of the acoustic radiative surface and the RF radiative surface. Since undesirable side effects (such as skin-burning) typically occur in proximity to the RF radiative surface, in some embodiments cooling of one or both of the radiative surfaces allows cooling of a potentially affected surface.

In some embodiments, a device further comprises cooling-fluid channels in thermal communication with at least one of the acoustic radiative surface and the RF radiative surface. In some such embodiments, the cooling-fluid channels are in thermal communication with at least one of the sonotrode and the RF applicator.

During use of the device, such cooling-fluid channels can be functionally associated with an appropriately configured cooling device or cooling assembly that drives a cooling fluid through the cooling-fluid channels, thereby cooling at least one of the acoustic radiative surface and the RF radiative surface. In some embodiments, the device further comprises a cooling assembly functionally associated with the cooling-fluid channels configured, when activated, to drive a cooling fluid through the cooling-fluid channels, thereby cooling at least one of the acoustic radiative surface and the RF radiative surface.

In some embodiments, a cooling assembly is activatable during at least one of activation of the ultrasound transducer and of an RF energy source functionally-associated with the RF applicator.

In some embodiments, in addition to including a cooling assembly to cool a radiative surface or in addition to being configured for use with a cooling assembly to cool a radiative surface, a device includes an RF energy source or is configured to be functionally-associated with an RF energy source configured in accordance with the teachings of U.S. Pat. No. 7,630,774. When such an RF energy source is activated to generate RF waves to implement the teachings herein, such an RF energy source allows the surface to remain at a substantially lower temperature than deeper layers of the volume of material, reducing the incidence of undesirable side-effects.

In some embodiments, a device as described herein is devoid of a cooling assembly and/or is not configured to be functionally associated with a cooling assembly but includes an RF energy source or is configured to be functionally-associated with an RF energy source configured in accordance with the teachings of U.S. Pat. No. 7,630,774 allowing a surface to remain at a substantially lower temperature than deeper layers of the volume of tissue when the RF energy source is activated.

Acoustic Waves

The ultrasound transducer, the sonotrode and the acoustic radiative surface are configured to generate and direct acoustic waves of any suitable characteristics (frequencies, energy and modes of use) that are effective for an intended use, for example for treatment of subcutaneous fat, for example as disclosed in US 2011/0213279. The ultrasound transducer is any suitable ultrasound transducer, for example similar to that disclosed in US 2011/0213279. The sonotrode is any suitable sonotrode, for example similar to that disclosed in US 2011/0213279. The acoustic radiative surface is any suitable acoustic radiative surface, for example similar to that disclosed in US 2011/0213279.

In some embodiments, the ultrasound transducer, the sonotrode and the acoustic radiative surface are together configured so that the acoustic energy is conveyed by longitudinal acoustic waves, for example as disclosed in US 2011/0213279.

In some embodiments, the ultrasound transducer, the sonotrode and the acoustic radiative surface are together configured so that acoustic energy is conveyed by transverse ultrasonic mechanical waves, for example as disclosed in US 2011/0213279.

In some embodiments, the ultrasound transducer, the sonotrode and the acoustic radiative surface are together configured so that acoustic energy is conveyed by both transverse and longitudinal ultrasonic mechanical waves, for example as disclosed in US 2011/0213279.

In some embodiments, the ultrasound transducer, the sonotrode and the acoustic radiative surface are together configured so that acoustic energy is alternatingly conveyed by transverse and longitudinal ultrasonic mechanical waves, for example as disclosed in US 2011/0213279.

RF Waves

The RF applicator is configured to direct RF waves generated by a functionally-associated RF energy source and the RF radiative surface is configured to form a unipolar RF field therefrom, the RF waves having any suitable characteristics (frequency, energy, modes of use) that are effective for the intended use in accordance with the teachings herein, for example for treatment of subcutaneous fat as disclosed in U.S. Pat. No. 7,630,774. An RF energy source that is a component of the device or that the device is configured to be functionally-associated with is any suitable RF energy source, for example similar to that disclosed in U.S. Pat. No. 7,630,774. The RF applicator is any suitable RF applicator, for example similar to that disclosed in U.S. Pat. No. 7,630,774. The RF radiative surface is any suitable RF radiative surface, for example similar to that disclosed in U.S. Pat. No. 7,630,774.

That said and as discussed with reference to the method according to the teachings herein, since the preferred mode of depositing thermal energy is dielectric heating with a unipolar RF field, in some embodiments the RF applicator is configured to direct RF waves and the RF radiative surface is configured to form a unipolar RF field therefrom having a frequency of not less than 2 MHz, not less than 4 MHz and in some embodiments not less than 10 MHz, and in typical preferred embodiments, between 10 MHz and 100 MHz.

In some embodiments the configuration of the RF applicator and of the RF radiative surface is for RF waves having a frequency in an Industrial, Scientific and Medical frequency band, e.g., selected from the group consisting of 13.560 MHz±7 kHz, 27.120 MHz±163 kHz, 40.68 MHz±20 kHz, 2.45 GHz±50 MHz, 5.800 GHz±75 MHz, 24.125 GHz±125 MHz, 6.780 MHz±15 kHz, 61.25 GHz±250 MHz, 122.5 GHz±500 MHz, 245 GHZ±1 GHz, 433.92 MHz±870 and 915 MHz±13 MHz.

In some embodiments the configuration of the RF applicator and of the RF radiative surface is for RF waves having a frequency of 13.560 MHz±7 kHz, 27.120 MHz±163 kHz, 915 MHz±13 MHz, but most especially 40.68 MHz±20 kHz.

In some embodiments, the device further comprises an RF energy source functionally associated with the RF applicator configured, when activated, to generate RF waves sufficient so that the unipolar RF field formed at the RF radiative surface is sufficient to deposit an effective amount of thermal energy into the volume of material. By "effective amount" is meant an amount sufficient to cause or initiate a desired effect in the volume of material. Such an RF energy source is configured to generate RF waves of any suitable RF frequency. That said, as discussed with reference to the method according to the teachings herein, since the preferred mode of depositing thermal energy is dielectric heating with a unipolar RF field, in some embodiments it is preferred that the RF energy source is configured to generate RF waves having a frequency of not less than 2 MHz, not less than 4 MHz and in some embodiments not less than 10 MHz, and in typical preferred embodiments, between 10 MHz and 100 MHz, especially 13.560 MHz±7 kHz, 27.120 MHz±163 kHz, 915 MHz±13 MHz, but most especially 40.68 MHz±20 kHz.

In some embodiments, the surface is a skin surface, the material is hypodermis and the RF applicator and the RF radiative surface are together configured so that a formed unipolar RF field deposits an effective amount of thermal energy sufficient to heat the volume of hypodermis. In some such embodiments, the effective amount of thermal energy deposited is sufficient to raise (and in some embodiments maintain) the temperature of a volume of hypodermis to a temperature of between 42° C. and 48° C., or even to a temperature of between 42° C. and 46° C.

As noted above any suitable ultrasound transducer, sonotrode and acoustic radiative surface may be used in implementing a device as disclosed herein. Further, as also noted above any suitable RF energy source, RF applicator and RF radiative surface may be used in implementing a device as disclosed herein.

That said and also as noted above, in some embodiments, at least a portion of the acoustic radiative surface constitutes at least a portion and even all of the RF radiative surface, and in some embodiments, the ultrasound radiative surface constitutes the RF radiative surface. In some such embodiments, the sonotrode and the RF applicator are the same component.

In the art (for example, in US 2011/0213279), it is known that to effectively convey acoustic energy into a material, a sonotrode is preferably a solid rigid component, having an acoustic impedance as close as possible to that of the material. For example to treat biological tissue having an acoustic impedance of 1.3-2.0 MRayls (kg/(sm$^2$×10$^6$)), a sonotrode is typically glass or porcelain (~13 MRayls) or a metal having a low acoustic impedance like aluminum and aluminum alloys (~17 MRayls). It is also known to coat the acoustic radiative surface of a sonotrode with an acoustic matching layer, a layer of a sufficient thickness of a material having an acoustic impedance between that of the sonotrode and the material into which the acoustic energy is conveyed. When the material is biological tissue, suitable acoustic matching layers are layers of PVDF (polyvinylidene fluoride, 4.2 MRayl) or PTFE (polytetrafluoroethylene, 3 MRayl), typically 1 to 50 micrometers thick, preferably 5 to 20 micrometers thick.

The Inventors have recognized that although RF applicators known in the art are typically flexible components unsuitable for use as a sonotrode (e.g., a printed circuit board such as described in U.S. Pat. No. 7,452,358), it is possible to use a component that is substantially a solid rigid (that is sufficiently rigid for conveying acoustic energy) mass of electrically-conductive material as both an RF applicator and as a sonotrode: the electrical conductivity of the material renders such a combined component suitable for use as a waveguide to guide RF waves and the rigidity of the material renders such a combined component suitable for conveying acoustic energy.

Thus, in some embodiments of a device in accordance with the teachings herein, an RF applicator is substantially a solid rigid mass of electrically-conductive material. In some such embodiments, the RF applicator is a single integrally-formed component. Typical such materials include aluminum (17.3 MRayls), titanium (27 MRayls), silver (38 MRayls), copper (44.6 MRayls), gold (63.8 MRayls) and alloys thereof.

Particularly, in US 2011/0213279 is disclosed a sonotrode which description, details, and modes of use are included by reference as if fully set-forth herein. The Inventors have recognized that in some embodiments, a similar such sonotrode can be appropriately modified for use also as an RF applicator in accordance with the teachings herein. In some such embodiments, the sonotrode is configured (inter alia, in terms of shape and dimensions) to be suitable for conveying both longitudinal and transverse acoustic energy, as described in US 2011/0213279.

As noted above, in some embodiments a device as described herein comprises or is functionally associated with a cooling assembly configured to cool, when activated, at least one of the acoustic radiative surface and the RF radiative surface, for example to reduce the incidence of undesired side-effects such as burning of a surface such as of skin. In some such embodiments, the cooling assembly comprises cooling-fluid channels in thermal communication with at least one of the sonotrode and the RF applicator. For example, in some embodiments, especially when the RF applicator is a solid rigid mass of conductive material, the cooling-fluid channels are in thermal communication with a portion of the RF applicator. Since the RF applicator is of a solid electrically-conductive material, thermal conduction through the RF applicator is efficient. In such embodiments, when the cooling assembly is activated, cooling fluid (e.g., a gas or liquid, typically a liquid such as water or an aqueous solution) flows through the cooling-fluid channels, cooling the portion of the RF applicator, and by conduction through the solid mass, also the RF radiative surface.

In some embodiments, the cooling-fluid channels pass through a component separate from the RF applicator that contacts a portion of the RF applicator and are thereby in thermal communication with the RF applicator and the RF radiative surface.

In some embodiments, the cooling-fluid channels pass through bulk of the RF applicator and are thereby in thermal communication with the RF applicator and the RF radiative surface. In some such embodiments, it is important that the dimensions and location of the cooling-fluid channels be such as to not interfere with the functioning of the RF applicator as a sonotrode, e.g., by causing internal reflection of acoustic waves or by substantially reducing the structural integrity of the RF applicator.

It is known that an RF radiative surface of an RF applicator may optionally comprise a layer of a dielectric material as an electrical insulator to prevent conduction of current therethrough, into biological tissue being treated, as taught in U.S. Pat. No. 7,630,774. As noted above, it is also known that an acoustic radiative surface of a sonotrode comprises an acoustic matching layer to increase the efficiency of conveying of acoustic energy from the sonotrode into the biological tissue. The Inventors have recognized that some acoustic matching layers are dielectric and can therefore also serve as an electrical insulator to prevent conduction of current therethrough. Accordingly, in some embodiments (especially where at least a portion of the acoustic radiative surface constitutes at least a portion of the RF radiative surface) a portion of the acoustic radiative surface constituting at least a portion of the RF radiative surface comprises a layer of a dielectric material, the layer having a thickness sufficient to substantially prevent conduction of current therethrough when a functionally-associated RF energy source is activated and the layer also suitable for functioning as an acoustic matching layer when the ultrasound transducer is activated. Suitable materials from which such a layer is fashioned include PVDF (polyvinylidene fluoride, 4.2 MRayl) and PTFE (polytetrafluorethylene, 3 MRayl), typically 1 to 50 micrometers thick, preferably 5 to 20 micrometers thick.

In some embodiments, the sonotrode and the RF applicator are the same component fashioned of a solid rigid mass of aluminum or aluminum alloy, similar to the solid aluminum sonotrode disclosed in US 2011/0213279. The electrical conductivity of aluminum and alloys thereof is relatively low (compared to silver, gold and copper), but despite this has been surprisingly found to be sufficient for acting as a waveguide to implement the teachings herein. The acoustic impedance of aluminum and alloys thereof (~17.3 MRayls) is relatively high compared to that of biological tissue, but is significantly lower than that of other materials having a high electrical conductivity (e.g., silver, gold and copper). An additional advantage of aluminum and alloys thereof is the layer of aluminum oxide (alumina, $Al_2O_3$) that naturally forms on a surface thereof. The aluminum oxide forms a natural dielectric layer that functions as an electrical insulator to prevent conduction of current therethrough, into biological tissue being treated and burning of the biological tissue. Aluminum oxide has an exceptionally high acoustic impedance (40.6 MRayls) but it has been found that the aluminum oxide layer naturally forming on a solid rigid mass of aluminum such as a sonotrode as described herein is typically thin enough (about 4 nm) to not substantially interfere with the conveying of acoustic energy from an ultrasound transducer to a volume of hypodermis. That said, in some embodiments a thicker aluminum oxide layer is applied (e.g., by anodization or by sputtering) to reduce the chance of burning of tissue and/or conduction of current therethrough. Typically, such a thicker aluminum oxide layer is not more than 75 micrometers thick, not more than 50 micrometers thick and even not more than 40 micrometers thick. In some such embodiments, such a thicker aluminum oxide layer is between 5 micrometers and 15 micrometers (e.g., 10 micrometers) thick. It has been surprisingly been found that such a thick layer of aluminum oxide does not substantially adversely affect the ability of a radiative surface to direct acoustic waves through a skin surface when the RF applicator functions as a sonotrode in accordance with the teachings herein.

In some such embodiments, the radiative surface is coated with an acoustic matching layer (e.g., PVDF or PTFE) on the aluminum oxide layer. Such double layer coating improves the acoustic coupling of the acoustic radiative surface and tissue and also assists in preventing conduction of electrical current therethrough and/or burning of tissue, especially if the aluminum oxide layer is cracked or otherwise damaged. In such embodiments, the aluminum oxide layer is not more than 75 micrometers thick, not more than 50 micrometers thick, not more than 40 micrometers thick, and even between 5 micrometers and 15 micrometers (e.g., 10 micrometers) while the acoustic matching layer applied to the surface of the aluminum oxide layer (e.g., of PVDF or PTFE) is typically 1 to 50 micrometers thick, preferably 5 to 20 micrometers thick.

First Embodiment of a Device According to the Teachings Herein

Figure 1B:
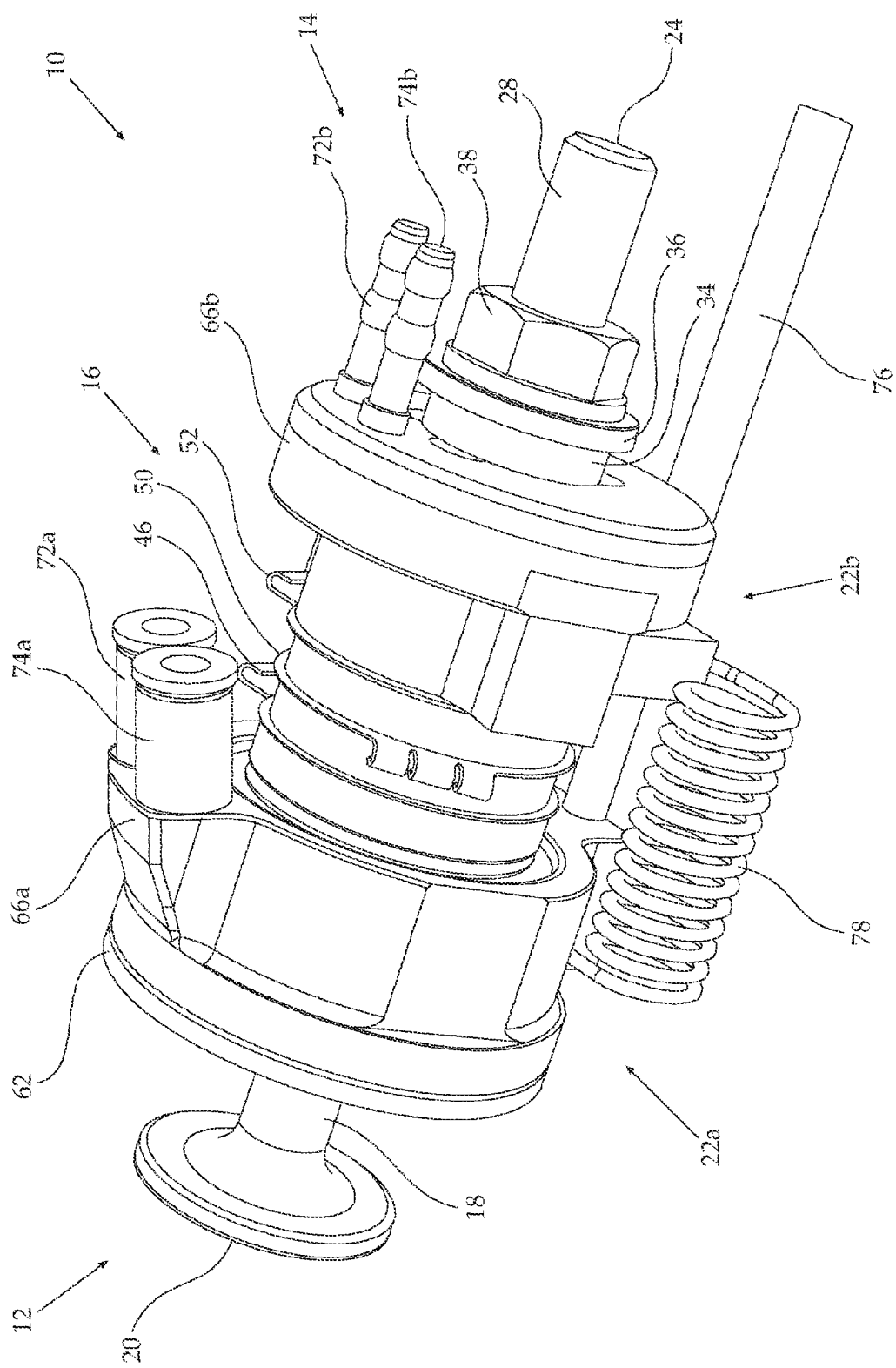
FIG. 1B depicts the embodiment of the device of FIG. 1A fully assembled, in perspective from a proximal end.
Figure 1C:
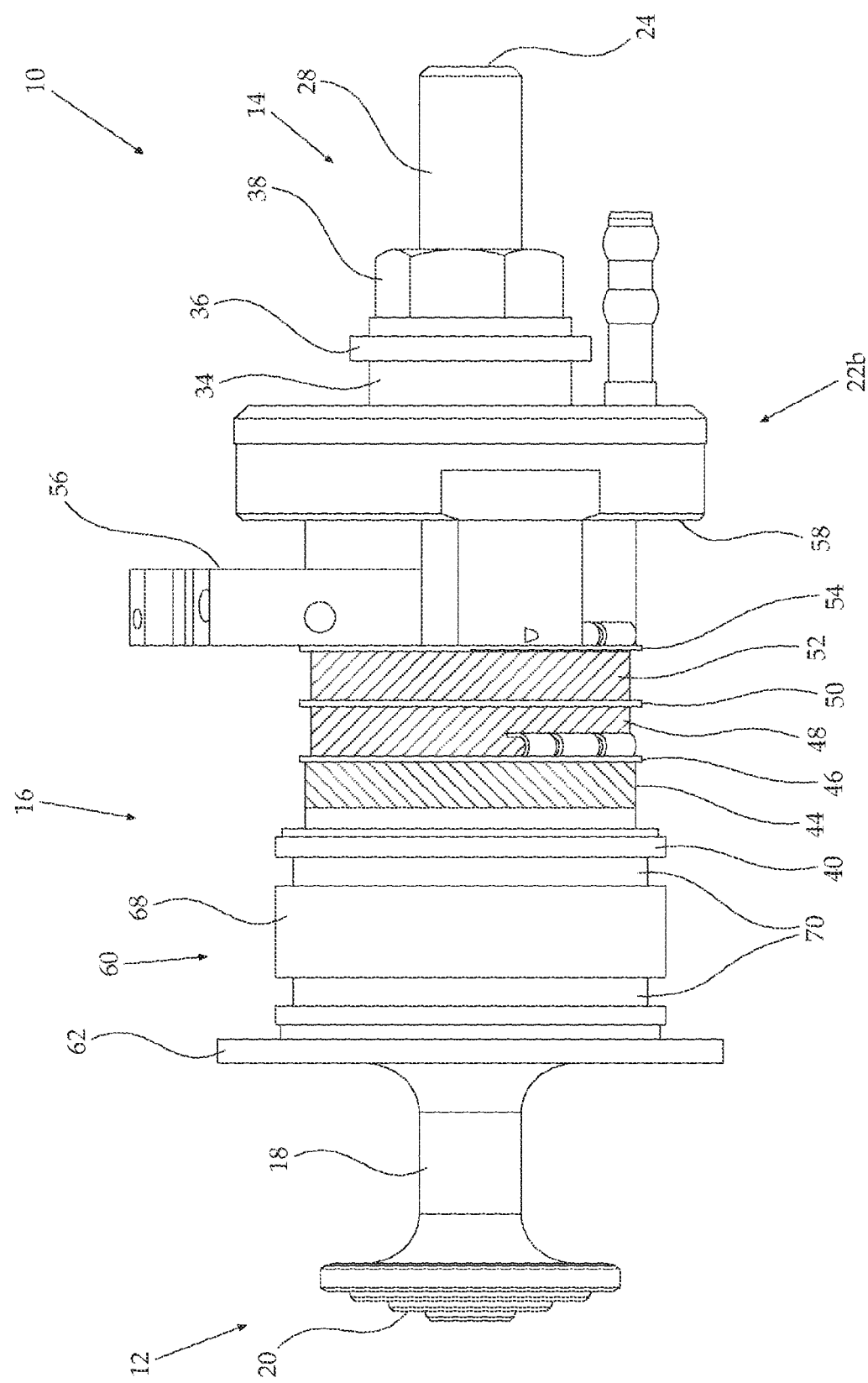
FIG. 1C depicts the embodiment of the device of FIGS. 1A and 1B, with some components removed to show details of construction from the side.
Figure 1D:
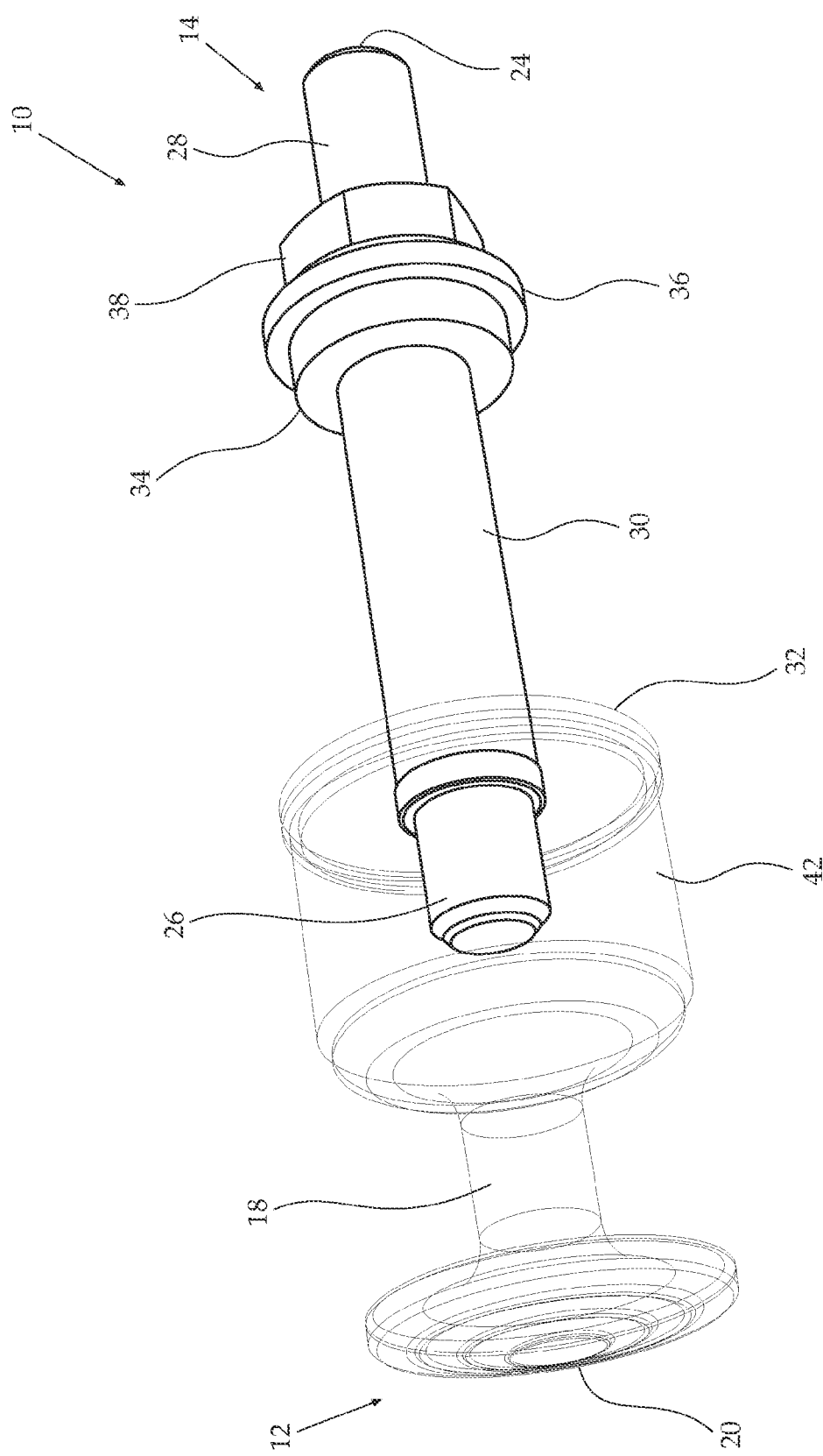
FIG. 1D depicts the embodiment of the device of FIGS. 1A-1C, with some components removed to show details of construction, in perspective from a distal end.
Figure 1E:
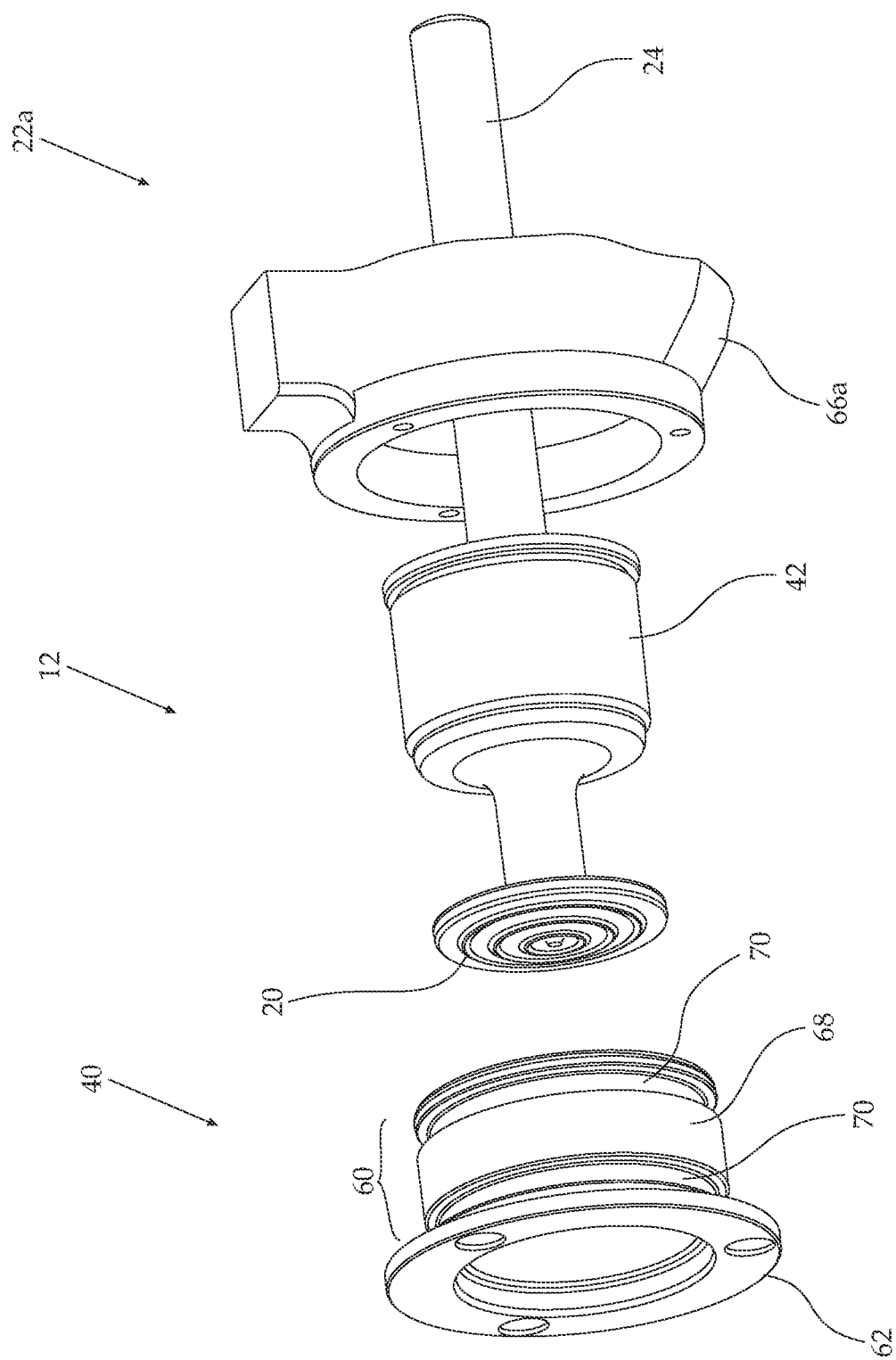
FIG. 1E depicts the embodiment of the device of FIGS. 1A-1D, with some components removed to show details of construction, in perspective from a distal end.
Figure 1F:
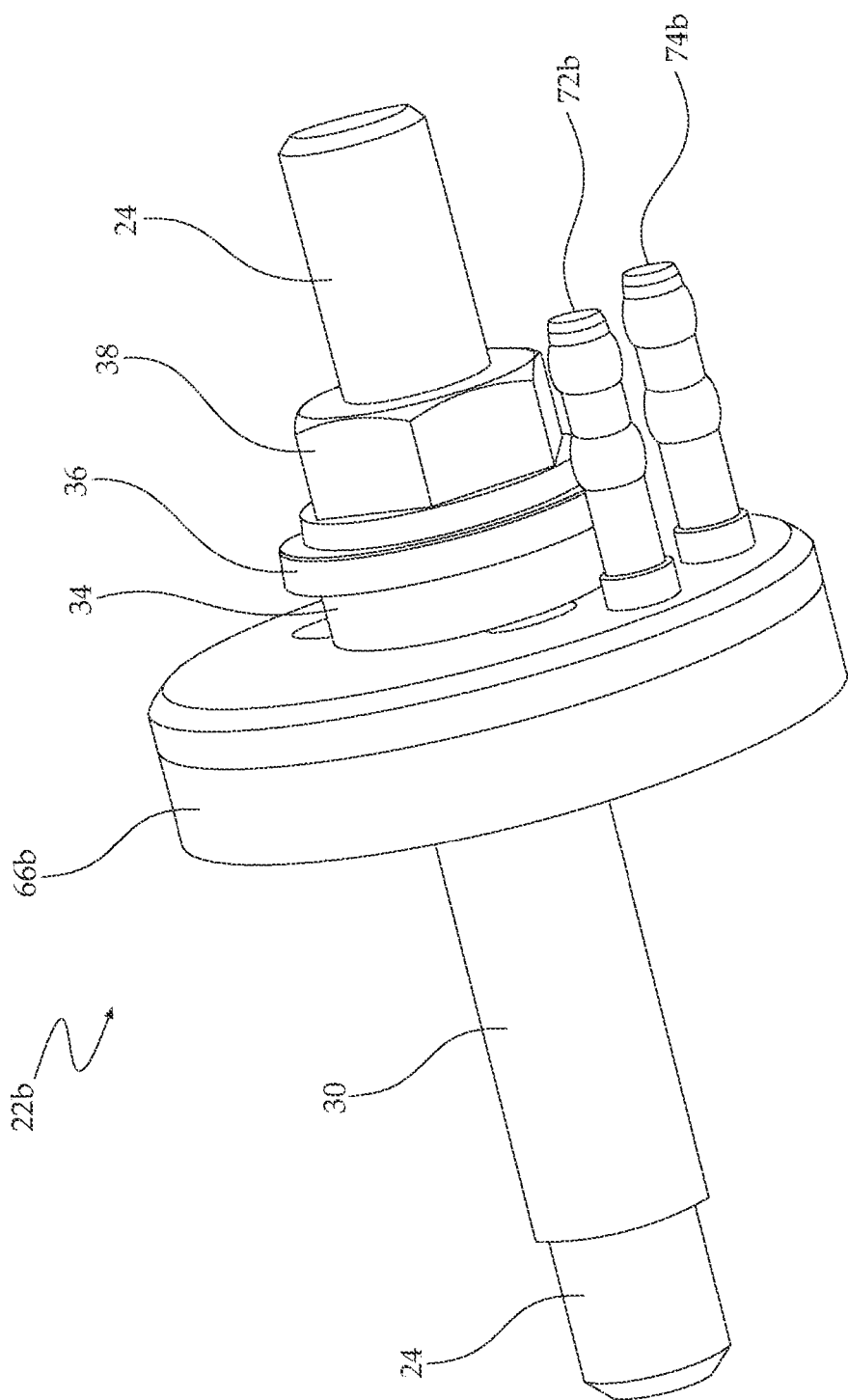
FIG. 1F depicts the embodiment of the device of FIGS. 1A-1E, with some components removed to show details of construction, in perspective from a proximal end.

An embodiment of a device for the treatment of a volume of material with energy through a surface, specifically for treatment of subcutaneous fat as described herein, device 10, is schematically depicted in FIGS. 1A-1F. In FIG. 1A, device 10 is depicted fully assembled, viewed in perspective from a distal end 12. In FIG. 1B, device 10 is depicted fully assembled, viewed in perspective from a proximal end 14. In FIG. 1C, device 10 is depicted with some components removed to show details of construction, viewed from the side. In FIGS. 1D, 1E and 1F, device 10 is depicted with some components removed to show details of construction, viewed in perspective.

Device 10 is a probe configured for concurrently depositing an effective amount of thermal energy into a volume of hypodermis with a unipolar RF field through a skin surface and for conveying an effective amount of acoustic energy into the volume of hypodermis through a skin surface in accordance with embodiments of the method according to the teachings herein. Specifically, the concurrent depositing of the effective amount of thermal energy and of the effective amount of acoustic energy is sufficient to initiate a process leading to a reduction of the amount of fat in the volume of hypodermis.

Device 10 comprises a rigid stacked ultrasound transducer 16 with a distally-located sonotrode 18 having an acoustic radiative surface 20 and a cooling assembly made up of two independently-operable portions, distal cooling assembly 22a and proximal cooling assembly 22b. A cooling-fluid channel of distal cooling assembly 22a is in thermal communication with sonotrode 18 and, through the bulk of sonotrode 18, acoustic radiative surface 20.

Sonotrode 18 also functions as an RF applicator so that in device 10 the sonotrode and the RF applicator are the same component and so that at least a portion of acoustic radiative surface 20 constitutes at least a portion of the RF radiative surface, specifically, acoustic radiative surface 20 constitutes the RF radiative surface of the RF applicator of device 10.

Sonotrode/RF Applicator

Sonotrode/RF applicator 18 is fashioned from a single solid homogenous rigid block of aluminum alloy (Al 7075), substantially as described in US 2011/0213279, allowing functioning both as an RF applicator and to direct acoustic waves through radiative surface 20.

Substantially all exposed surfaces of sonotrode/RF applicator 18, and particularly radiative surface 20 are coated with a native layer of alumina formed by exposure of aluminum metal to atmospheric oxygen. The alumina layer is dielectric and of sufficient thickness to substantially prevent conduction of current through radiative surface 20 when an RF energy source functionally-associated with sonotrode/RF applicator 18 is activated. The alumina layer is sufficiently thin so as not to substantially impede passage of acoustic waves through radiative surface 20.

Radiative surface 20 includes a plurality of concentric circular ridges, similar to that described in US 2011/0213279. The diameter of radiative surface 20 is 4 cm, allowing device 10 to concurrently convey an effective amount of acoustic energy and/or deposit an effective amount of thermal energy to a cylinder of tissue having a diameter of up to about 4 cm and to a depth of up to about 2 cm deep, that is to say a volume of hypodermis of up to about 25 $cm^3$.

Stacked Ultrasound Transducer

The components and assembly of stacked ultrasound transducer 16 are clearly depicted in FIG. 1, especially FIG. 1C and FIG. 1D.

In FIG. 1D, sonotrode/RF applicator 18 is depicted as transparent, showing central shaft 24 which a distal end 26 thereof is screwed into and thereby secured into a hole in the proximal end of sonotrode/RF applicator 20. For clarity, not depicted are the threads on distal end 26 or the counter-threads in the hole in sonotrode/RF applicator 20.

Intimately contacting and surrounding most of the length of central shaft 24 is electrically insulating sleeve 30 of PTFE (a tube having a wall thickness of 1-2 mm) which distal end contacts a proximal face 32 of sonotrode/RF applicator 20.

At a proximal end 28 of central shaft 24 is a sapphire insulating washer 34 having a larger diameter than insulating sleeve 30. Insulating washer 34 is partially surrounded by a rubber washer 36.

A brass nut 38 is screwed over threads (not depicted) on proximal end 28 of central shaft 24 to the extent that brass nut 38 presses insulating washer 34 and insulating sleeve 30 tightly together and against proximal face 32 of sonotrode/RF applicator 20.

In FIG. 1C, the components of device 10 that are stacked along central shaft 24 between sonotrode/RF applicator 18 and insulating washer 34, and electrically insulated from central shaft 24 are depicted. From proximal to sonotrode/RF applicator 18 in a proximal direction, the components are: a brass sleeve 40 (which distal end cups and is in intimate contact with a proximal end 42 of sonotrode/RF applicator 18), a sapphire insulator ring 44, a distal transducer plate 46, a distal piezoelectric ceramic ring 48, a central transducer plate 50, a proximal piezoelectric ceramic ring 52, a proximal transducer plate 54, negative contact 56 and a proximal cooling assembly 22b. The stacked components all have a central hole dimensioned to intimately fit over insulating sleeve 30, preventing any substantial movement of the components perpendicularly to the axis of central shaft 24. The thicknesses of the stacked components are such that when device 10 is fully assembled, brass nut 38 presses against insulating washer 34 that presses against a proximal face 58 of proximal cooling assembly 22b so that the stacked components are all tightly pressed together and against proximal face 32 of sonotrode/RF applicator 18, preventing any substantial movement of the components.

Cooling Assembly

As noted above, device 10 comprises a cooling assembly made up of two independently-operable portions, distal cooling assembly 22a and proximal cooling assembly 22b.

Distal Cooling Assembly

Surrounding a proximal portion 60 of brass sleeve 40 and held in place against a flange 62 of brass sleeve 40 with screws 64 is distal cooling assembly 22a including a brass distal cooling envelope 66a. A distal cooling channel is defined by a portion 68 of an outer surface of proximal portion 60 of brass sleeve 40 between two O-rings (not depicted) placed in grooves 70, the two O-rings, and an inner surface of distal cooling envelope 66a. The distal cooling channel is in fluid communication with a distal cooling fluid inlet 72a and a distal cooling fluid outlet 74a. Cooling fluid entering through cooling fluid inlet 72a is forced through the distal cooling channel to contact portion 68 of the outer surface of proximal portion 60 of brass sleeve 40 to cool brass sleeve 40 and, by thermal conduction, sonotrode/RF applicator 18 and radiative surface 20.

Proximal Cooling Assembly

Proximal cooling assembly 22b is stacked along central shaft 24 surrounding insulating sleeve 30. Proximal cooling assembly 22b includes a hollow proximal cooling envelope 66b that defines a proximal cooling channel in fluid communication with a proximal cooling fluid inlet 72b and a proximal cooling fluid outlet 74b. Cooling fluid entering through cooling fluid inlet 72b is forced through the proximal cooling channel to cool the walls of proximal cooling envelope 66b, and by thermal conduction, negative contact 56, proximal transducer plate 54, proximal piezoelectric ceramic ring 52, central transducer plate 50, distal piezoelectric ceramic ring 48 and distal transducer plate 54.

Coaxial Cable and Coil

A coaxial cable 76 and a copper coil 78 provide functional association of device 10 with an RF energy source. Coaxial cable 76 is any (commercially-available) coaxial cable able to direct RF waves for operating device 10 as described above. Copper coil 78 is a coil selected to function as a high-impedance inductor for RF electrical currents (e.g., 40 MHz) but as a conductor for lower frequency electrical currents (e.g., less than 200 kHz)

The outer conductive shield of coaxial cable 76 is in direct electrical contact with negative contact 56 so that negative contact 56 and proximal transducer plate 54 are ground for an RF current from coaxial cable 76. The outer conductive shield of coaxial cable 76 is in electrical contact with distal cooling envelope 66a, brass sleeve 40 and sonotrode/RF applicator 18 through coil 78.

The inner conductive core of coaxial cable 76 is in direct electrical contact with distal cooling envelope 66a, brass sleeve 40 and sonotrode/RF applicator 18 to direct RF waves from an RF energy source to sonotrode/RF applicator 18.

As is clear to one skilled in the art, the stacked construction of ultrasound transducer 16 constitutes a capacitor, most significantly across sapphire insulator ring 44 between distal transducer plate 46 and the proximal face of brass sleeve 40. Such a capacitor absorbs power from RF waves, potentially preventing conduction of a sufficiently powerful RF waves to sonotrode/RF applicator 18. To avoid such an effect, copper coil 78 acts as an inductor at radiofrequencies (e.g., 40 MHz) located in parallel to the capacitor, lowering the impedance of the circuit and thus preventing the capacitor from absorbing energy from RF waves. For lower frequencies, e.g., less than 200 kHz such as ultrasound, coil 78 acts as a short circuit between sonotrode/RF applicator 18 and negative contact 56.

Operation of Device 10

As device 10 is substantially a probe, for use device 10 must be functionally associated with other devices to function: an RF energy source to generate and provide RF waves through coaxial cable 24, an ultrasound power source to generate and provide an appropriately-modulated alternating current to plates 46, 50 and 54 of ultrasound transducer 16 and a cooling fluid pump to generate, drive and recycle cooling fluid through cooling-fluid channels of cooling assembly 22a and 22b.

To generate and convey acoustic energy through radiative surface 20, an ultrasound power source is functionally associated with ultrasound transducer 16, by electrically connecting a positive lead of the ultrasound power source to central transducer plate 50 and electrically connecting a ground lead of the ultrasound power source to distal transducer plate 48 and to proximal transducer plate 52. As known in the art of "sandwich type" ultrasound transducers, ultrasound transducer 16 is activated when the ultrasound power source generates an appropriately-modulated current alternating at a desired frequency, typically of between 1 kV and 1.5 kV alternating at between 100 kHz and 160 kHz, generating an alternating electrical field between the pairs of transducer plates 46/50 and 50/54. Piezoelectric ceramic rings 48 and 52 located in the alternating electrical field between the pairs of transducer plates axially expand and relax at the frequency of the electric field, producing ultrasonic vibrations that are transmitted through the rigid structure of ultrasound transducer 16, including radiative surface 20 of sonotrode/RF applicator 18 as acoustic waves. If radiative surface 20 is acoustically coupled with a surface of a material such as a skin surface, radiative surface 20 directs the acoustic waves into the volume of material through the surface to convey acoustic energy into the volume of the material. Depending on the frequency of the current from the ultrasound power source, sonotrode/RF applicator 18 directs longitudinal (~100 kHz) or transverse (~160 kHz) acoustic waves through radiative surface 20, as described in US 2011/0213279.

To deposit thermal energy in the volume of material through radiative surface 20, an RF energy source is functionally associated with sonotrode/RF applicator 18 through coaxial cable 76. The RF energy source is activated to generate RF waves (e.g., 40.68 MHz±20 kHz) that are directed by coaxial cable 76 through distal cooling envelope 66a, brass sleeve 40 to sonotrode/RF applicator 18. Sonotrode/RF applicator 18 directs the RF waves to radiative surface 20 where a unipolar RF field having a frequency of the RF current is formed. The unipolar RF field deposits an effective amount of thermal energy in the volume of material by dielectric heating.

The ultrasound power source and the RF energy source can activated separately or concurrently (including simultaneously), allowing both separate and concurrent (including simultaneous) conveying of acoustic energy and depositing of thermal energy in a volume of material through radiative surface 20.

Second Embodiment of a Device According to the Teachings Herein

Figure 2:
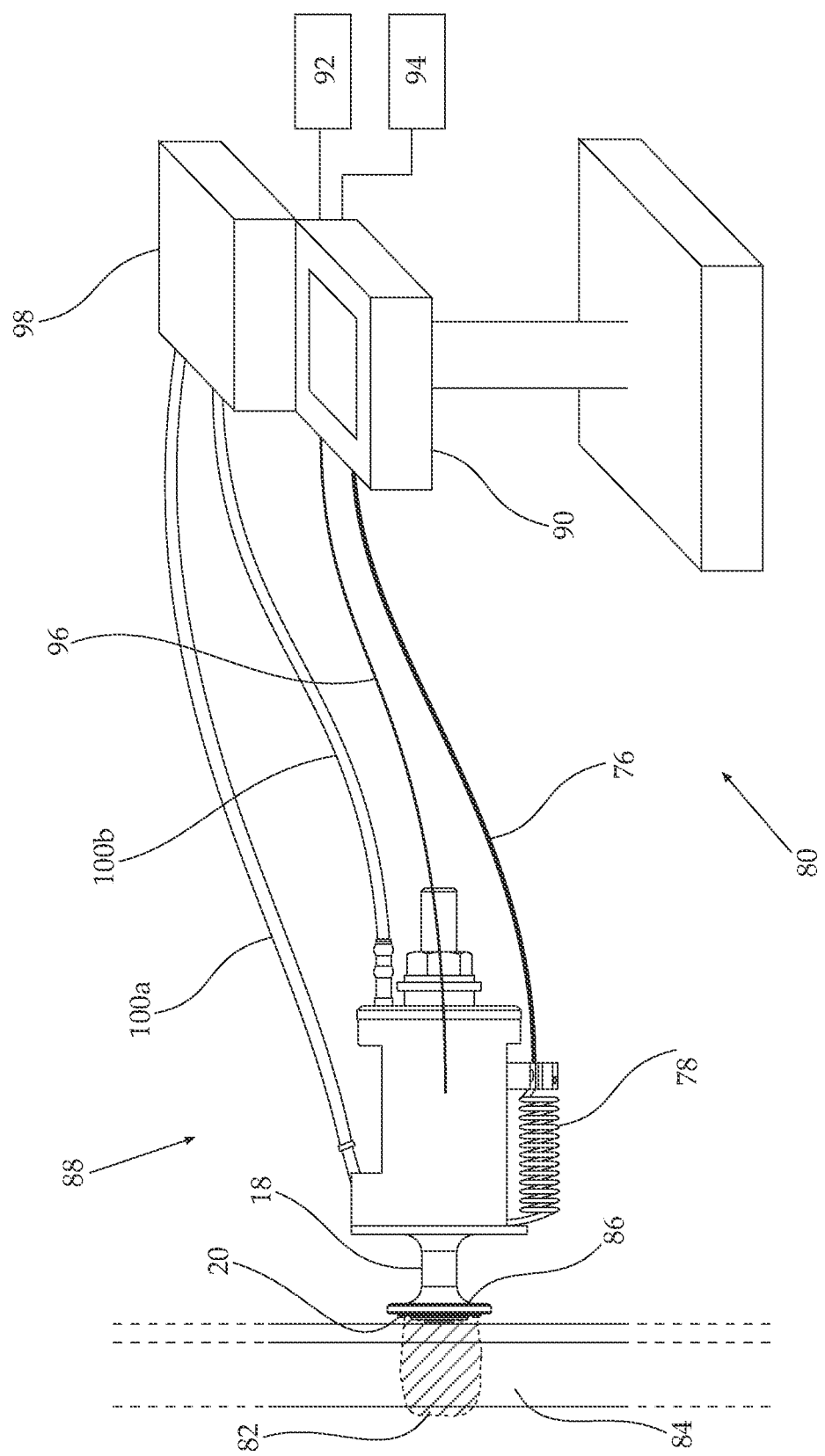
FIG. 2 schematically depicts a second embodiment of a device suitable for treatment of a volume of material such as hypodermis according to the teachings herein.

An additional embodiment of a device for the treatment of a volume of material with energy through a surface, specifically for the treatment of subcutaneous fat as described herein, device 80, is schematically depicted in FIG. 2 during use for treatment of a volume 82 of tissue including subcutaneous fat 84 through a skin surface 86. It is important to note, particularly with regard to FIG. 2, that some objects are not depicted to scale for clarity.

Device 80 comprises a probe 88, substantially identical to device 10 described with reference to FIG. 1, and additionally comprises a controller 90, an RF energy source 92 (e.g., such as described in U.S. Pat. No. 7,630,774) functionally associated with a sonotrode/RF applicator 18 of probe 88 through controller 90 and coaxial cable 76 and an ultrasound power source 94 (e.g., such as described in US 2011/0213279) functionally associated with an ultrasound transducer 16 through controller 90 and leads 96.

Device 80 also comprises cooling fluid pump 98, that is functionally associated with the cooling fluid channels of the cooling assemblies of probe 88 through the cooling fluid and outlets, cooling fluid pump 98 configured to produce and drive water chilled to between 0° and 20° C. as a cooling fluid through the cooling-fluid channels via conduits 100a and 100b, standard flexible cooling-fluid conduits known in the art.

In FIG. 2, device 80 is depicted where a radiative surface 20 of a sonotrode/RF applicator 18 of probe 88 is coupled (by direct contact after application of petroleum jelly) to a skin surface 86 of a human subject.

For use in treating subcutaneous fat, a user activates controller 90 and selects a mode of operation.

The user can select a first "ultrasonic only" mode of use where only the ultrasound transducer of device 80 is activated (and not RF energy source 92) for treatment of volume of tissue 82 with acoustic energy alone, as known in the art, for example as described in US 2011/0213279. As known in the art, the user selects the various acoustic energy parameters (intensity, frequency, transverse and/or longitudinal waves) through controller 90. Controller 90 activates ultrasound power source 94 to provide an appropriately-modulated electronic signal (in accordance to the user-selected parameters) to the ultrasound transducer, thereby activating the ultrasound transducer to convey an effective amount of acoustic energy into volume 82 of tissue through skin surface 86, leading to a desired effect.

Alternatively, the user can select a second "RF only" mode of use where only RF energy source 92 is activated (and not the ultrasound transducer) for treatment of with thermal energy alone, as known in the art, for example as described in U.S. Pat. No. 7,630,774. As known in the art, the user selects the various RF parameters (e.g., intensity, frequency) through controller 90. Controller 90 activates RF energy source 92 to provide appropriately-modulated RF waves (in accordance to the user-selected parameters) that are directed by sonotrode/RF applicator 18 to radiative surface 20 to form a unipolar RF field at radiative surface 20 that deposits an effective amount of thermal energy through skin surface 86 to volume of tissue 82. Consequently and as known in the art, the temperature of the subcutaneous fat in volume 82 of tissue rises (e.g., temperature of between 42° C. and 48° C.), leading to a desired effect.

Alternatively, the user can select a third "concurrent" mode of use where RF energy source 92 is activated (substantially as described above) concurrently with activation of the ultrasound transducer (substantially as described above). By concurrent activation is meant in accordance with any of the embodiments of the method of treatment as described above (including simultaneous and alternating activation). Due to the fact that ultrasound radiative surface 20 constitutes the RF radiative surface, the intersection of the volume of tissue in which the thermal energy is deposited and the volume of tissue into which acoustic energy is conveyed, and consequently the volume 82 to which an effective amount of thermal energy is deposited concurrently with conveying of an effective amount of acoustic energy is maximal, depending in the user-defined settings, up to 25 cm$^3$.

As is known in the art, the user can move radiative surface 20 to portions of skin surface of the treated subject different from surface 86 to treat volumes of hypodermis different from volume 82.

Independently of controller 90, at any time and during operation of device 80 in any mode, a user optionally also activates cooling fluid pump 98 and selects a cooling fluid temperature (typically between 15° and 20° C.). Cooling fluid pump 98 operates, chilling a cool fluid (water) and driving the chilled cooling fluid through conduits 100a and 100b.

Cooling fluid pump 98 drives the chilled cooling fluid through conduit 100a into the distal cooling channel of probe 88. As the distal cooling fluid channel is in thermal communication therewith, the cooling fluid cools sonotrode/RF applicator 18, radiative surface 20 and thereby skin surface 86, numbing the skin and reducing the chance of undesirable side-effects such as burning of the skin surface.

In the embodiments described above with reference to the figures, radiative surface 20 of sonotrode/RF applicator 18 includes a plurality of concentric circular ridges as described in US 2011/0213279. In some, non-depicted, related embodiments, the radiative surface includes other features, for example as described in US 2011/0213279, such as multiple discontinuous surfaces, plurality of protrusions, plurality of vertical ridges.

In the embodiments described above with reference to the figures, sonotrode/RF applicator 18 has a shape and dimensions allowing delivery of longitudinal ultrasonic waves at ~100 kHz and delivery of transverse ultrasonic waves at ~160 kHz through radiative surface 20, as described in US 2011/0213279. In some embodiments, a sonotrode/RF applicator has a different shape and/or dimensions for delivering different frequencies of longitudinal and/or transverse ultrasonic waves.

In the embodiments described above with reference to the figures, radiative surface 20 of sonotrode/RF applicator 18 is coated with a native (about 4 nm thick) electrically-insulating layer of dielectric alumina. In some embodiments, a radiative surface of an RF applicator is coated with a thicker electrically-insulating layer, for example, not more than 50 micrometers, not more than 40 micrometers, more typically between 5 micrometers and 15 micrometers (e.g., 10 micrometers) thick layer of alumina (e.g. applied by anodization or sputtering). It has been surprisingly been found that such thick layers of alumina do not substantially adversely affect the ability of a radiative surface 20 to direct acoustic waves through a skin surface when the RF applicator functions as a sonotrode in accordance with the teachings herein.

In some embodiments, a radiative surface 20 is coated (additionally to an alumina layer) with a second layer (e.g., of PTFE or PVDA) that functions as an acoustic matching layer when an ultrasound transducer 16 is activated, and in some embodiments the second layer functions also as an additional layer to prevent conduction of current through radiative surface 20 when a functionally-associated RF energy source such as 92 is activated.

In some embodiments, a radiative surface 20 is coated (instead of the alumina layer) with a layer (e.g., of PTFE or PVDA) that functions both as an acoustic matching layer when an ultrasound transducer 16 is activated and as a dielectric layer to prevent conduction of current through radiative surface 20 when a functionally-associated RF energy source such as 92 is activated.

In the embodiments described above with reference to the figures, coil 78 functions as an inductor to prevent loss of energy from RF waves generated by an RF energy source. In some embodiments, other types of inductors are used instead.

In the embodiments described above with reference to the figures, the outer conductive shield of coaxial cable 76 is in direct electrical contact with negative contact 56 so that negative contact 56 and proximal transducer plate 54 are ground for an RF current from coaxial cable 76. In some embodiments, the outer conductive shield of coaxial cable 76 is in direct electrical contact (alternately or additionally) with other components of a transducer, e.g., a central transducer plate such as 50 or a distal transducer plate such as 46.

In the embodiments described above with reference to the figures, devices 10 and 80, and especially the respective radiative surfaces 20 of sonotrodes/RF applicators 18 are configured to concurrently convey an effective amount of acoustic energy and deposit an effective amount of thermal energy to a cylinder of tissue having a volume of up to 25 cm$^3$. In some embodiments, the maximal size of such a volume of tissue is greater or lesser, in some embodiment up to 56 cm$^3$.

In the embodiment described above with reference to FIG. 2, controller 90 of device 80 is configured to allow a user to use device 80 in three modes: activation of the ultrasound transponder for acoustic energy treatment alone, activation of RF energy source 92 for thermal energy treatment alone, and concurrent activation for concurrent treatment.

In some embodiments, a device is configured for mandatory concurrent activation of an ultrasound transponder and of an RF energy source.

In some embodiments, such a device is configured to allow a user to use the device in two modes: activation of the ultrasound transponder for conveying acoustic energy only or concurrent activation of the RF energy source for thermal energy deposition with activation of the ultrasound transponder for conveying acoustic energy.

In some embodiments, such a device is configured to allow a user to use the device in two modes: activation of the RF energy source for RF energy treatment only or concurrent activation of the RF energy source for thermal energy deposition with activation of the ultrasound transponder for conveying acoustic energy.

In the embodiment described above with reference to the Figures, devices 10 and 80 comprise a cooling assembly including two independently-operable portions 22a and 22b, 22a being in thermal communication with sonotrode/RF applicator 18. In some (non-depicted) embodiments, such devices comprise a cooling assembly including more than two independently-operable portions or only one portion. In some (non-depicted) embodiments, such devices are devoid of a cooling assembly.

In the embodiment described above with reference to the Figures, devices 10 and 80 comprise a cooling assembly including a cooling-fluid channel in thermal communication with sonotrode/RF applicator 18. In some (non-depicted) embodiments, such devices comprise a cooling assembly including at least one cooling-channel that passes through the sonotrode/RF applicator 18. In some (non-depicted) embodiments, such a device comprises a cooling assembly devoid of cooling-channels.

In the embodiment described above with reference to the Figures, devices 10 and 80 and the components thereof are together configured for the generation and directing longitudinal ultrasonic mechanical waves and of transverse ultrasonic mechanical waves. In some (non-depicted) embodiments, such devices are configured for generation and directing only longitudinal ultrasonic mechanical waves. In some (non-depicted) embodiments, such devices are configured for generation and directing only transverse ultrasonic mechanical waves.

The teachings herein have been described in the context of the treatment of subcutaneous fat in the hypodermis through the skin. In some embodiments, the teachings herein are applied to the treatment of a volume of a material through a surface other than a skin surface and/or a material other than biological tissue.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

The invention claimed is:

1. A device suitable for treatment of a volume of hypodermis with energy through a skin surface, the device comprising:
    a sonotrode having an acoustic radiative surface and an ultrasound transducer functionally associated with the sonotrode, said ultrasound transducer configured, when activated, to generate acoustic waves that are directed by said acoustic radiative surface into the volume of hypodermis for conveying an effective amount of acoustic energy into the volume of hypodermis for aesthetic modification thereof; and
    an RF energy source and an RF applicator having an RF radiative surface, said RF applicator functionally associable with the RF energy source, said RF applicator being configured to direct RF waves generated by an activated RF energy source to said RF radiative surface to form a unipolar RF field for depositing an effective amount of thermal energy in the volume of hypodermis for aesthetic modification thereof,
wherein the device is configured for activation of said ultrasound transducer and said RF energy source independently or concurrently;
said sonotrode and said RF applicator are the same component whereby the acoustic radiative surface and the RF radiative surface are coupled to the same portion of the skin surface; and
the radiative surface common to the sonotrode and the RF applicator comprises a layer of dielectric material configured to serve as an insulator to prevent conduction of current through the RF radiative surface when coupled to an active RF energy source and as an acoustic matching layer when coupled to an active ultrasound transducer.

2. The device of claim 1, wherein said RF applicator is configured to direct RF waves having a frequency of not less than 2 MHz and said RF radiative surface is configured to form a unipolar RF field having a frequency of not less than 2 MHz.

3. The device of claim 1, wherein said sonotrode and said RF applicator are configured so that said volume of hypodermis treated at any one time is between 7 cm^3 and 56 cm^3.

4. The device of claim 1, wherein said RF applicator is a solid rigid mass of electrically-conductive material.

5. The device of claim 1, wherein the device has multiple operating modes wherein the acoustic energy source and the RF energy source are each selectively activated either continuously or intermittently.

6. The device of claim 5, wherein the RF energy source is activated periodically at a rate of not less than 0.2 Hz.

7. The device of claim 1, further comprising a cooling assembly configured, when activated, to cool at least one of said acoustic radiative surface and said RF radiative surface.

8. The device of claim 1, wherein said ultrasound transducer, said sonotrode and said acoustic radiative surface are together configured so that said acoustic energy is conveyed by at least one of longitudinal waves and transverse waves coupled into the hypodermis.

9. The device of claim 8, wherein both longitudinal and transverse waves are coupled into the hypodermis either alternately or concurrently.

10. A method of using the device of claim 1 for cosmetic treatment of human skin, wherein the device is controlled to raise the temperature of the volume of hypodermis to above 42° C. and to maintain it between 42° C. and 48° C. for a period of time.

* * * * *